(12) United States Patent
Haga et al.

(10) Patent No.: US 8,124,760 B2
(45) Date of Patent: Feb. 28, 2012

(54) PYRIDYL-TRIAZOLOPYRIMIDINE DERIVATIVE OR ITS SALT, PESTICIDE CONTAINING IT AND ITS PRODUCTION PROCESS

(75) Inventors: Takahiro Haga, Kusatsu (JP); Hirohiko Kimura, Kusatsu (JP); Masayuki Morita, Kusatsu (JP); Tsuyoshi Ueda, Kusatsu (JP); Toshihiko Ueki, Kusatsu (JP); Kazuhisa Kiriyama, Kusatsu (JP); Kotaro Yoshida, Kusatsu (JP); Taku Hamamoto, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 242 days.

(21) Appl. No.: 12/526,520

(22) PCT Filed: Feb. 7, 2008

(86) PCT No.: PCT/JP2008/052475
§ 371 (c)(1),
(2), (4) Date: Aug. 10, 2009

(87) PCT Pub. No.: WO2008/099902
PCT Pub. Date: Aug. 21, 2008

(65) Prior Publication Data
US 2010/0087452 A1    Apr. 8, 2010

(30) Foreign Application Priority Data

Feb. 15, 2007  (JP) .................................. 2007-034371

(51) Int. Cl.
*C07D 487/00* (2006.01)
(52) U.S. Cl. ..................................................... 544/263
(58) Field of Classification Search ........................ None
See application file for complete search history.

(56) References Cited

U.S. PATENT DOCUMENTS

| 4,209,621 A | 6/1980 | Dusza et al. |
| 4,444,774 A | 4/1984 | Dusza et al. |
| 4,562,192 A | 12/1985 | Wagner |

FOREIGN PATENT DOCUMENTS

| WO | 02 02563 | 1/2002 |
| WO | 2004 082383 | 9/2004 |

OTHER PUBLICATIONS

"7-(pyridin-2-yl)-[1,2,4]triazolo[1,5-a]pyrimidine", Bionet Research Ltd., p. 1, XP002478905, RN: 320416-38-04, (2001).
Selby, T. P. et al., "7-Phenyl-1,2,4-triazolo [1,5-α] pyrimidines and Related Heterocycles a New Family of Bleaching Herbicides", Synthesis and Chemistry of Agrochemicals III, pp. 91-102, XP009099658, (1992).
Petrich, S. A. et al., "The Application of Unsymmetrical Vinylogous Iminium Salts and Related Synthons to the Preparation of Monosubstituted Triazolo[1,5-a]pyrimidines", Tetrahedron, vol. 50, No. 42, pp. 12113-12124, XP002478904, (1994).
Wermuth, C. G. et al. "Molecular Variations Based on Isosteric Replacements", The Practice of Medicinal Chemistry, pp. 203-237, XP002190259, (1996).

*Primary Examiner* — Jeffrey Murray
(74) *Attorney, Agent, or Firm* — Oblon, Spivak, McClelland, Maier & Neustadt, L.L.P.

(57) ABSTRACT

To provide a novel pesticide. The present invention provides a pesticide containing a pyridyl-triazolopyrimidine derivative represented by the formula (I) or its salt as an active ingredient: wherein $R_1$ is substitutable alkyl, substitutable cycloalkyl, substitutable alkenyl, substitutable alkynyl, halogen, cyano, aryl, a heterocyclic group which may be substituted by alkyl, $OR_2$, $S(O)_n R_3$ or $NR_4 R_5$; $R_2$ is hydrogen, alkyl, alkenyl, alkynyl, haloalkyl, alkoxyalkyl, acetyl or aryl; $R_3$ is alkyl or acetyl; $R_4$ is hydrogen or alkyl; $R_5$ is hydrogen, alkyl or the like; X is alkyl, alkenyl, alkynyl, halogen, haloalkyl, cyano, nitro or the like; m is an integer of from 1 to 4; and n is an integer of from 0 to 2.

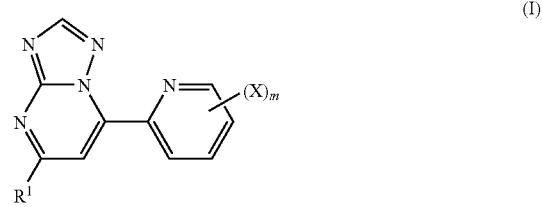

(I)

11 Claims, No Drawings

PYRIDYL-TRIAZOLOPYRIMIDINE DERIVATIVE OR ITS SALT, PESTICIDE CONTAINING IT AND ITS PRODUCTION PROCESS

TECHNICAL FIELD

The present invention relates to a pesticide containing a novel pyridyl-triazolopyrimidine derivative or its salt as an active ingredient.

BACKGROUND ART

WO2004/082383 discloses use of triazolopyrimidine derivatives having a specific chemical structure as a nematicide. However, these compounds are different from the compounds of the present invention in the chemical structure. Further, WO2002/02563 discloses a method of preventing or treating growth of cancerous tumor cells and associated diseases, which comprises applying an effective amount of a triazolopyrimidine derivative to a mammal. However, it failed to disclose the compounds of the present invention and use of the compounds of the present invention as a pesticide.

DISCLOSURE OF THE INVENTION

Object to be Accomplished by the Invention

For many years, many pesticides have been used, but many of them have various problems such that the effects are inadequate, their use is restricted as pests have acquired resistance, etc. Accordingly, it is desired to develop a novel pesticide substantially free from such problems, for example, a pesticide capable of controlling various pests which create problems in agricultural and horticultural fields or a pesticide capable of controlling pests parasitic on animals.

Means to Accomplish the Object

The present inventors have conducted various studies on pyridyl-triazolopyrimidine derivatives in an effort to find a superior pesticide. As a result, they have found that a novel pyridyl-triazolopyrimidine derivative has an extremely high pesticidal effect against pests at a low is dose and at the same time has safety to crop plants, the natural enemy to pests or mammals, and have accomplished the present invention.

Namely, the present invention relates to a pyridyl-triazolopyrimidine derivative represented by the formula (I) or its salt:

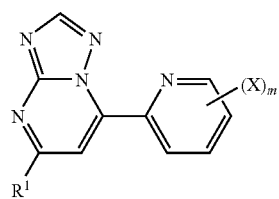

(I)

wherein $R^1$ is hydrogen, alkyl which may be substituted by A, cycloalkyl which may be substituted by A, alkenyl which may be substituted by A, alkynyl which may be substituted by A, halogen, cyano, aryl, a heterocyclic group which may be substituted by alkyl, $OR^2$, $S(O)_nR^3$ or $NR^4R^5$; $R^2$ is hydrogen, alkyl, alkenyl, alkynyl, haloalkyl, alkoxyalkyl, acetyl or aryl; $R^3$ is alkyl or acetyl; $R^4$ is hydrogen or alkyl; $R^5$ is hydrogen, alkyl, acetyl, $CH_2CH_2OR^2$ or $CH_2CN$; A is halogen, $OR^2$, $S(O)_nR^3$, $NR^4R^5$, cyano, alkyl, cycloalkyl, aryl, a heterocyclic group, $SCH_2COOR^2$ or $-CH(CN)_2$; X is alkyl, alkenyl, alkynyl, aryl, halogen, haloalkyl, cyano, nitro, $NR^4R^5$, $S(O)_nR^3$, $COR^2$ or $COOR^2$; m is an integer of from 1 to 4; and n is an integer of from 0 to 2; provided that 7-(3-chloro-5-(trifluoromethyl)pyridin-2-yl)-[1,2,4]triazolo[1,5-a]pyrimidine is excluded.

The present invention further relates to a pesticide containing the pyridyl-triazolopyrimidine derivative of the formula (I) or its salt as an active ingredient, a method for controlling a pest by applying it, and its production process.

EFFECTS OF THE INVENTION

A pesticide containing the pyridyl-triazolopyrimidine derivative of the above formula (I) or its salt as an active ingredient, has a very high pesticidal effect against pests at a low dose.

BEST MODE FOR CARRYING OUT THE INVENTION

When m is an integer of from 2 to 4, the respective X's may be the same or different.

As the halogen or halogen as the substituent in the formula (I), an atom of fluorine, chlorine, bromine or iodine may be mentioned. The number of halogens as the substituents may be 1 or more, and if more, the respective halogens may be the same or different. Further, the positions for substitution of such halogens may be any positions.

The alkyl in the formula (I) may be linear or branched. As its specific example, $C_{1-6}$ alkyl such as methyl, ethyl, propyl, isopropyl, butyl, tert-butyl, pentyl or hexyl may be mentioned.

As the cycloalkyl in the formula (I), $C_{3-6}$ cycloalkyl such as cyclopropyl, cyclobutyl, cyclopentyl or cyclohexyl may, for example, be mentioned.

The alkenyl in the formula (I) may be linear or branched. As its specific example, $C_{2-6}$ alkenyl such as vinyl, 1-propenyl, allyl, isopropenyl, 1-butenyl, 1,3-butadienyl or 1-hexenyl may be mentioned.

The alkynyl in the formula (I) may be linear or branched. As its specific example, $C_{2-6}$ alkynyl such as ethynyl, 2-butynyl, 2-pentynyl, 3-methyl-1-butynyl, 2-penten-4-ynyl or 3-hexynyl may be mentioned.

As the aryl in the formula (I), $C_{6-10}$ aryl such as phenyl or naphthyl may, for example, be mentioned.

The heterocyclic group in the formula (I) includes a fused heterocyclic group in addition to a monocyclic heterocyclic group. The monocyclic heterocyclic group may, for example, be a 3-membered heterocyclic group such as oxiranyl; a 5-membered heterocyclic group such as furyl, tetrahydrofuryl, thienyl, pyrrolyl, pyrrolinyl, pyrrolidinyl, dioxolanyl, oxazolyl, isoxazolyl, thiazolyl, isothiazolyl, imidazolyl, imidazolinyl, imidazolidinyl, pyrazolyl, pyrazolinyl, pyrazolidinyl, triazolyl, oxadiazolyl, thiadiazolyl or tetrazolyl; or a 6-membered heterocyclic group such as pyranyl, pyridyl, piperidinyl, dioxanyl, oxazinyl, morpholinyl, thiazinyl, pyridazinyl, pyrimidinyl, pyrazinyl, piperazinyl or triazinyl. Among such monocyclic heterocyclic groups, preferred is a 5- or 6-membered monocyclic heterocyclic group containing from 1 to 4 atoms of at least one type selected from the group consisting of O, S and N. The fused heterocyclic group may, for example, be benzofuranyl, isobenzofuranyl, dihydrobenzofuranyl, dihydroisobenzofuranyl, benzothienyl, isobenzothienyl, dihydrobenzothienyl, dihydroisobenzothienyl, tetrahydrobenzothienyl, indolyl, isoindolyl, benzoxazolyl, benzothiazolyl, indazolyl, benzimidazolyl, benzodioxolanyl, benzodioxanyl, chromenyl, chromanyl, isochromanyl, chromonyl, chromanonyl, quinolyl, isoquinolyl, cinnolinyl, phthalazinyl, quinazolinyl, quinoxalinyl, indolizinyl, quinolizinyl, imidazopyridyl, naphthyridinyl, pteridinyl, dihydrobenzoxazinyl, dihydrobenzoxazolinonyl, dihydrobenzoxazinonyl or benzothioxanyl. Among such fused heterocyclic groups, preferred is a 8- to 10-membered fused heterocyclic group containing from 1 to 4 atoms of at least one type selected from the group consisting of O, S and N.

The salt of the pyridyl-triazolopyrimidine derivative of the above formula (I) includes all kinds so long as they are agriculturally acceptable. For example, an ammonium salt such as a dimethylammonium salt or a triethylammonium salt; an inorganic acid salt such as a hydrochloride, a perchlorate, a sulfate or a nitrate, or an organic acid salt such as an acetate or a methanesulfonate, may be mentioned.

The pyridyl-triazolopyrimidine derivative of the above formula (I) may have optical isomers or geometrical isomers, and such isomers and mixtures thereof are both included in the present invention. In the present description, isomers are disclosed as mixtures, unless otherwise specified. Further, in the present invention, various isomers other than those mentioned above, may be included within the scope of the common knowledge in this technical field. Further, depending upon the type of such an isomer, the chemical structure may be different from the above-mentioned formula (I), but it is obvious to one skilled in the art that such a structure is in isomeric relation and thus falls within the scope of the present invention.

The pyridyl-triazolopyrimidine derivative of the above formula (I) or its salt can be produced by the following production processes [1] to [9] and in accordance with a usual method for producing a salt.

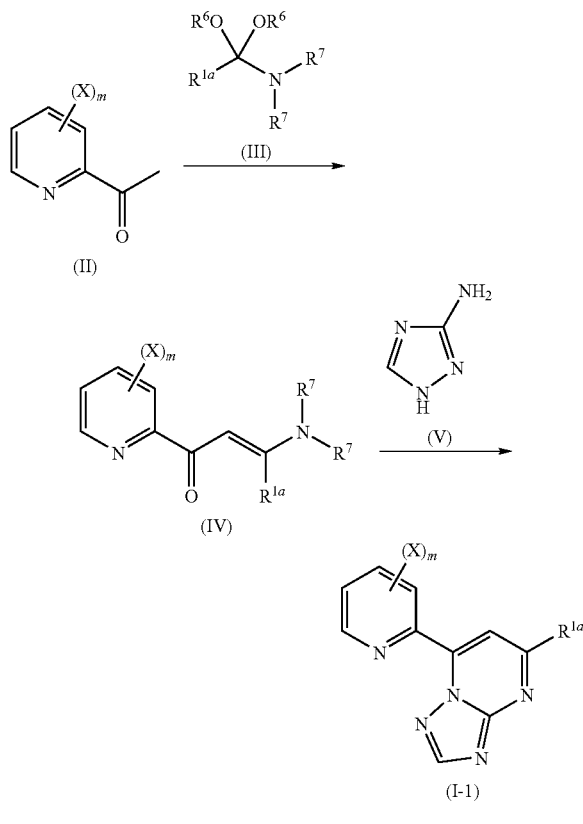

In production process [1], $R^{1a}$ is hydrogen, alkyl which may be substituted by A, cycloalkyl which may be substituted by A, alkenyl which may be substituted by A, alkynyl which may be substituted by A, aryl or a heterocyclic group which may be substituted by alkyl; each of $R^6$ and $R^7$ which are independent of each other, is alkyl; and A, X and m are as defined above.

The production process [1] comprises a first half reaction of condensing the compound of the formula (II) and the compound of the formula (III) to obtain the α,β-unsaturated ketone derivative of the formula (IV), and a second half reaction of condensing the compound of the formula (IV) and the compound of the formula (V) to obtain the [1,2,4]triazolo[1,5-a]pyrimidine derivative of the formula (I-1).

In the first half reaction in production process [1], the compound of the formula (III) may be used in a ratio of from 0.8 to 5 equivalent amount, preferably from 1 to 3 equivalent amount per mol of the compound of the formula (II). This reaction may usually be carried out in the presence of a solvent. The solvent may be any solvent so long as it is inert to the reaction, and it may, for example, be an alcohol such as methanol, ethanol, propanol or butanol; an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; an ester such as methyl acetate or ethyl acetate; a nitrile such as acetonitrile or propionitrile; an acid amide such as dimethylformamide, dimethylacetamide or N-methylpyrrolidinone; a sulfoxide such as dimethyl sulfoxide; a sulfone such as sulfolane; an amide phosphate such as hexamethylphosphoramide; a halogenated hydrocarbon such as chloroform, dichloromethane, carbon tetrachloride or 1,2-dichloroethane; or a solvent mixture thereof. The reaction temperature is usually from 80 to 200° C., preferably from 100 to 150° C. The reaction time is usually from 6 to 48 hours.

In the second half reaction in production process [1], the compound of the formula (V) may be used in a ratio of from 0.8 to 10 equivalent amount, preferably from 1 to 2.5 equivalent amount per mol of the compound of the formula (IV). This reaction may usually be carried out in the presence of a solvent. The solvent may be any solvent so long as it is inert to the reaction, and it may, for example, be a carboxylic acid such as acetic acid or propionic acid, an alcohol such as methanol, ethanol, propanol or butanol; an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; an ester such as methyl acetate or ethyl acetate; a nitrile such as acetonitrile or propionitrile; an acid amide such as dimethylformamide, dimethylacetamide or N-methylpyrrolidinone; a sulfoxide such as dimethyl sulfoxide; a sulfone such as sulfolane; an amide phosphate such as hexamethylphosphoramide; a halogenated hydrocarbon such as chloroform, dichloromethane, carbon tetrachloride or 1,2-dichloroethane; or a solvent mixture thereof, and a carboxylic acid is preferred. The reaction temperature is usually from 50 to 150° C., preferably from 80 to 120° C. The reaction time is usually from 0.5 to 100 hours.

PRODUCTION PROCESS [2]

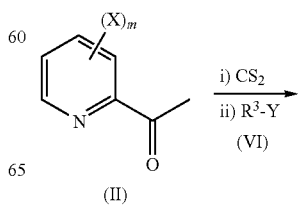

-continued

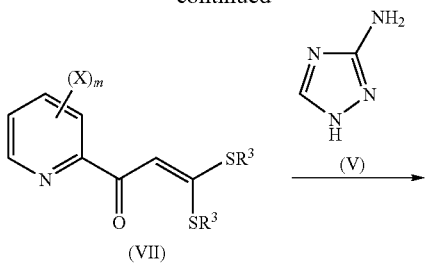

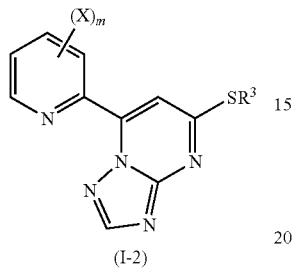

In production process [2], Y is halogen, and $R^3$, X and m are as defined above. As the halogen as Y, an atom of fluorine, chlorine, bromine or iodine may be mentioned.

Production process [2] comprises a first half reaction of reacting the compound of the formula (II), carbon disulfide and the compound of the formula (VI) to obtain the α,β-unsaturated ketone derivative of the formula (VII), and a second half reaction of condensing the compound of the formula (VII) and the compound of the formula (V) to obtain the [1,2,4]triazolo[1,5-a]pyrimidine derivative of the formula (I-2).

In the first half reaction in production process [2], each of carbon disulfide and the compound of the formula (VI) may be used in a ratio of from 0.8 to 5 equivalent amount, preferably from 1 to 3 equivalent amount per mol of the compound of the formula (II). This reaction may be carried out in the presence of a base and a solvent. The base may, for example, be an alkali metal hydride such as sodium hydride or potassium hydride; an alkali metal hydroxide such as sodium hydroxide or potassium hydroxide; an alkali metal such as sodium or potassium; an alkali metal alkoxide such as sodium methoxide, sodium ethoxide or potassium tertiary butoxide. The base may be used in a ratio of from 1 to 10 equivalent amount, preferably from 1 to 3 equivalent amount per mol of the compound of the formula (II). The solvent may be any solvent so long as it is inert to the reaction, and it may, for example, be the same solvent as used in the first half reaction in production process [1]. The reaction temperature is usually from 0 to 100° C., preferably from 10 to 50° C. The reaction time is usually from 6 to 48 hours.

In the second half reaction in production process [2], the compound of the formula (V) may be used in a ratio of from 0.8 to 5 equivalent amount, preferably from 1 to 3 equivalent amount per mol of the compound of the formula (VII). This reaction may usually be carried out in the presence of a base and a solvent. The base may, for example, be an alkali metal hydride such as sodium hydride or potassium hydride; an alkali metal hydroxide such as sodium hydroxide or potassium hydroxide; an alkali metal such as sodium or potassium; an alkali metal alkoxide such as sodium methoxide, sodium ethoxide or potassium tertiary butoxide; an alkali metal carbonate such as sodium carbonate or potassium carbonate; an alkali metal bicarbonate such as sodium bicarbonate or potassium bicarbonate; or an organic base such as triethylamine or pyridine. The base may be used in a ratio of from 1 to 5 equivalent amount, preferably from 1 to 3 equivalent amount per mol of the compound of the formula (V). The solvent may be any solvent so long as it is inert to the reaction, and it may, for example, be the same solvent as used in the first half reaction in production process [1]. The reaction temperature is usually from 100 to 200° C. The reaction time is usually from 0.1 to 10 hours.

PRODUCTION PROCESS [3]

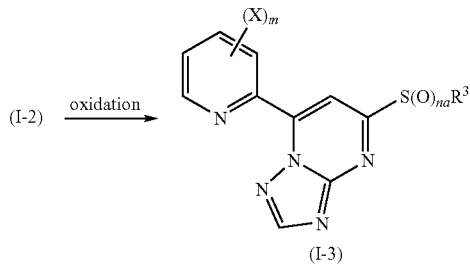

In production process [3], $R^3$, X and m are as defined above, and na is an integer of from 1 to 2.

In production process [3], the compound of the formula (I-2) and an oxidizing agent are reacted in the presence of a solvent to produce the [1,2,4]triazolo[1,5-a]pyrimidine derivative of the formula (I-3).

The oxidizing agent used for the above reaction may, for example, be hydrogen peroxide, peracetic acid or m-chloroperbenzoic acid. The solvent may be any solvent so long as it is inert to the reaction, and it may, for example, be a halogenated hydrocarbon such as chloroform, dichloromethane, carbon tetrachloride or 1,2-dichloroethane; a ketone such as acetone or dimethyl ethyl ketone; an ether such as diethyl ether, dipropyl ether, dibutyl ether, tetrahydrofuran or dioxane; a carboxylic acid such as acetic acid or propionic acid; or a solvent mixture thereof. The oxidizing agent may be used in a ratio of from 1 to 3 equivalent amount per mol of the compound of the formula (I-2). The reaction temperature is usually from room temperature to the reflux temperature. The reaction time is usually from 1 to 24 hours.

PRODUCTION PROCESS [4]

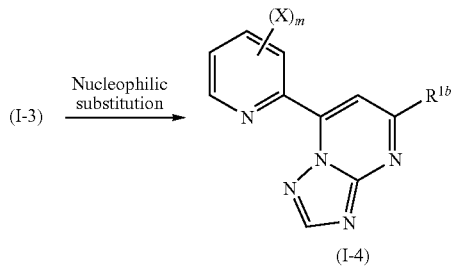

In production process [4], $R^{1b}$ is alkyl which may be substituted by A, cycloalkyl which may be substituted by A, alkenyl which may be substituted by A, alkynyl which may be substituted by A, halogen, cyano, aryl, a heterocyclic group which may be substituted by alkyl, $OR^2$ or $NR^4R^5$; and $R^2$, $R^4$, $R^5$, A, X and m are as defined above.

In production process [4], the compound of the formula (I-3) and a nucleophilic reagent are reacted in the presence of a solvent to produce the [1,2,4]triazolo[1,5-a]pyrimidine derivative of the formula (I-4).

The nucleophilic reagent may, for example, be an alkali metal alkoxide such as sodium methoxide or sodium ethoxide; an alkali metal mercaptide such as sodium methyl mercaptane; a primary or secondary amine such as methylamine, dimethylamine or piperidine; an organic metal reagent such as methyl magnesium bromide, ethyl magnesium bromide or phenyl magnesium bromide; or a fluorinating agent such as potassium fluoride, cesium fluoride or tetrabutylammonium fluoride. The nucleophilic reagent may be used in a ratio of from 1 to 5 equivalent amount, preferably from 1 to 3 equivalent amount per mol of the compound of the formula (I-3). The solvent may be any solvent so long as it is inert to the reaction, and it may, for example, be an alcohol such as methanol, ethanol, propanol or butanol, an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; an ester such as methyl acetate or ethyl acetate; a nitrile such as acetonitrile or propionitrile; an acid amide such as dimethylformamide, dimethylacetamide or N-methylpyrrolidinone; a sulfoxide such as dimethyl sulfoxide; or a solvent mixture thereof. The reaction temperature is usually from −100 to 50° C., preferably from −70 to 30° C. The reaction time is usually from one minute to 48 hours.

PRODUCTION PROCESS [5]

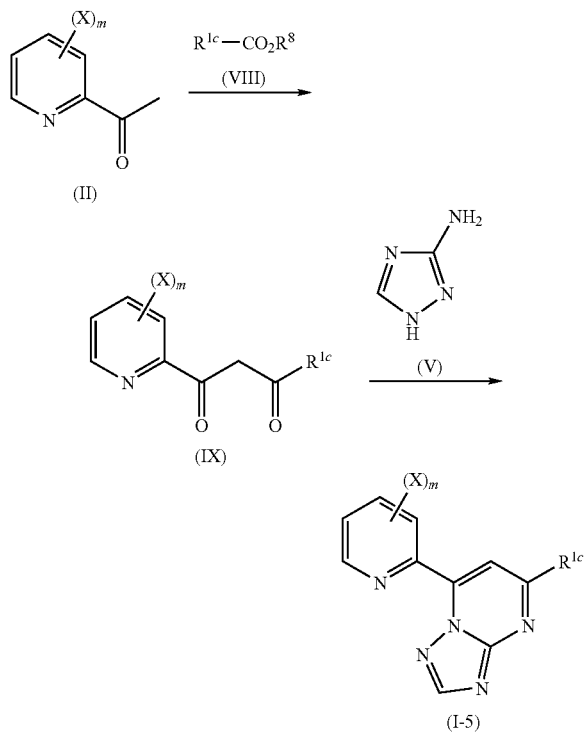

In production process [5], $R^{1c}$ is alkyl which may be substituted by A, cycloalkyl which may be substituted by A, alkenyl which may be substituted by A, alkynyl which may be substituted by A, aryl or a heterocyclic group which may be substituted by alkyl; $R^8$ is alkyl; and A, X and m are as defined above.

Production process [5] comprises a first half reaction of reacting the compound of the formula (II) with the compound of the formula (VIII) to obtain the compound of the formula (IX), and a second half reaction of condensing the compound of the formula (IX) and the compound of the formula (V) to obtain the [1,2,4]triazolo[1,5-a]pyrimidine derivative of the formula (I-5).

In the first half reaction in production process [5], the compound of the formula (VIII) may be used in a ratio of from 0.8 equivalent amount to a large excess amount, preferably from 1 to 10 equivalent amount per mol of the compound of the formula (II). This reaction may be carried out in the presence of a base and a solvent. The base may, for example, be the same base as used in the first half reaction in production process [2]. The base may be used in a ratio of from 1 to 5 equivalent amount, preferably from 1 to 2 equivalent amount per mol of the compound of the formula (II). The solvent may be any solvent so long as it is inert to the reaction, and it may, for example, be an alcohol such as methanol, ethanol, propanol or butanol, an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; an acid amide such as dimethylformamide, dimethylacetamide or N-methylpyrrolidinone; a sulfoxide such as dimethyl sulfoxide; a sulfone such as sulfolane; a halogenated hydrocarbon such as chloroform, dichloromethane, carbon tetrachloride or 1,2-dichloroethane; or a solvent mixture thereof, and an ether is preferred. The reaction temperature is usually from 0 to 70° C., preferably from 10 to 50° C. The reaction time is usually from 0.1 to 24 hours.

In the second half reaction in production process [5], the compound of the formula (V) may be used in a ratio of from 0.8 to 10 equivalent amount, preferably from 1 to 2.5 equivalent amount per mol of the compound of the formula (IX). This reaction may be carried out in the presence of a solvent. The solvent may be any solvent so long as it is inert to the reaction, and it may, for example, be the same solvent as used in the second half reaction in production process [1], and a carboxylic acid is preferred. When the compound of the formula (IX) is liquid at room temperature, the second half reaction in production process [5] may be carried out continuously without isolating the compound after the first half reaction in production process [5]. The reaction temperature is usually from 50 to 150° C., preferably from 80 to 120° C. The reaction time is usually from 0.5 to 100 hours.

PRODUCTION PROCESS [6]

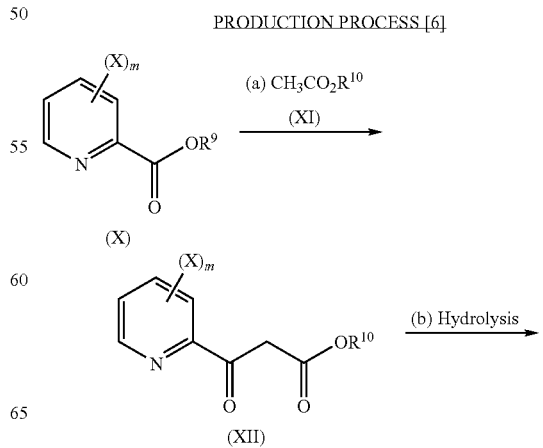

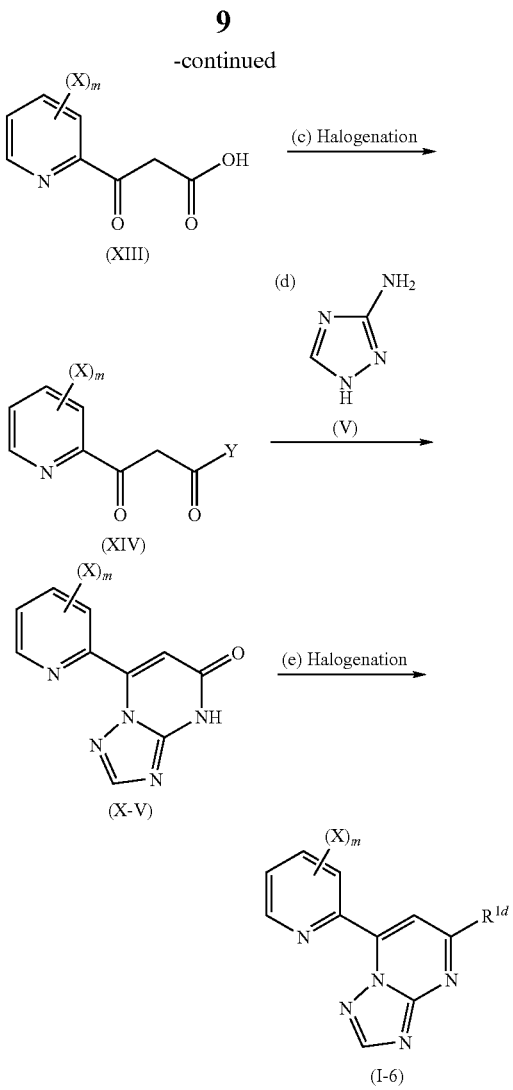

In production process [6], $R^{1d}$ is halogen; each of $R^9$ and $R^{10}$ which are independent of each other, is alkyl; and X, Y and m are as defined above. As the halogen as $R^{1d}$, an atom of fluorine, chlorine or bromine may be mentioned.

In production process [6], the compound of the formula (I-6) can be produced by the above reactions (a) to (e). The respective reactions will be described in detail below.

(a) The compound of the formula (XII) can be produced by reacting the compound of the formula (X) with the compound of the formula (XI) in the presence of a base and a solvent. The compound of the formula (XI) may be used in a ratio of from 0.8 equivalent amount to a large excess amount, preferably from 1 to 30 equivalent amount per mol of the compound of the formula (X). The base may, for example, be the same base as used in the first half reaction in production process [2]. The base may be used in a ratio of from 1 to 5 equivalent amount, preferably from 1 to 2 equivalent amount per mol of the compound of the formula (X). The solvent may be any is solvent so long as it is inert to the reaction, and it may, for example, be the same solvent as used in the first half reaction in production process [5], and an ether is preferred. The reaction temperature is usually from 0 to 70° C., preferably from 10 to 50° C. The reaction time is usually from 0.1 to 24 hours.

(b) The compound of the formula (XIII) can be produced by hydrolyzing the compound of the formula (XII) in the presence of a base and water. The base may be an alkali metal hydroxide such as sodium hydroxide or potassium hydroxide. The base may be used in a ratio of from 1 equivalent amount to a large excess amount per mol of the compound of the formula (XII). The reaction temperature is usually from 0 to 70° C., preferably from 10 to 50° C. The reaction time is usually from 0.1 to 24 hours.

(c) The compound of the formula (XIV) can be produced by reacting the compound of the formula (XIII) with a halogenating agent in the presence of a solvent. The halogenating agent may, for example, be thionyl chloride or oxalyl dichloride. The halogenating agent may be used in a ratio of from 1 to 5 equivalent amount, preferably from 1 to 2 equivalent amount per mol of the compound of the formula (XIII). The solvent may be any solvent so long as it is inert to the reaction, and it may, for example, be a halogenated hydrocarbon such as chloroform, dichloromethane, carbon tetrachloride or 1,2-dichloroethane. The reaction temperature is usually from 0 to 100° C., preferably from 10 to 50° C. The reaction time is usually from 0.1 to 24 hours.

(d) The 4,5-dihydro-5-oxo[1,2,4]triazolo[1,5-a]pyrimidine derivative of the formula (XV) can be produced by condensing the compound of the formula (XIV) and the compound of the formula (V). The compound of the formula (V) may be used in a ratio of from 0.8 to 10 equivalent amount, preferably from 1 to 2.5 equivalent amount per mol of the compound of the formula (XIV). This reaction may usually be carried out in the presence of a solvent. The solvent may be any solvent so long as it is inert to the reaction, and it may, for example, be the same solvent as used in the first half reaction in production process [5], and an acid amide is preferred. The reaction temperature is usually from 0 to 150° C., preferably from 20 to 100° C. The reaction time is usually from 0.5 to 100 hours.

(e) The 5-halo[1,2,4]triazolo[1,5-a]pyrimidine derivative of the formula (I-6) can be produced by reacting the compound of the formula (XV) with a halogenating agent. The halogenating agent may, for example, be thionyl chloride, phosphorus oxychloride or phosphorus oxybromide. The halogenating agent may be used in a ratio of from 1 to 20 equivalent amount, preferably from 1 to 8 equivalent amount per mol of the compound of the formula (XV). This reaction may usually be carried out in the presence of a solvent. The solvent may be any solvent so long as it is inert to the reaction, and it may, for example, be a halogenated hydrocarbon such as chloroform, dichloromethane, carbon tetrachloride or 1,2-dichloroethane. The reaction temperature is usually from 0 to 150° C., preferably from 20 to 100° C. The reaction time is usually from 0.1 to 24 hours.

PRODUCTION PROCESS [7]

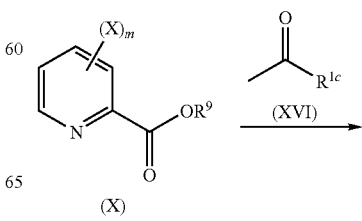

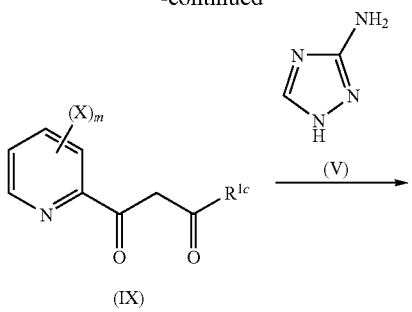

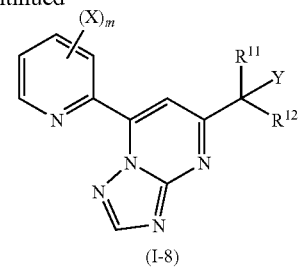

(I-8)

In production process [8], each of $R^{11}$ and $R^{12}$ which are independent of each other, is hydrogen, alkyl or cycloalkyl; and X, Y and m are as defined above.

In production process [8], the compound of the formula (I-7) and a halogenating agent are reacted in the presence of a solvent and a small amount of a radical initiator to produce the [1,2,4]triazolo[1,5-a]pyrimidine derivative of the formula (I-8). This reaction may be carried out, if necessary, under irradiation with light.

The halogenating agent may, for example, be N-chlorosuccinimide, N-bromosuccinimide or N-iodosuccinimide. The halogenating agent may be used in a ratio of from 1 to 5 equivalent amount, preferably from 1 to 2 equivalent amount per mol of the compound of the formula (I-7). The radical initiator may, for example, be benzoyl peroxide or azobisisobutylonitrile. The solvent may be any solvent so long as it is inert to the reaction, and it may, for example, be a halogenated hydrocarbon such as chloroform, dichloromethane, carbon tetrachloride or 1,2-dichloroethane. The reaction temperature is usually from 0 to 100° C., preferably from 10 to 80° C. The reaction time is usually from 0.1 to 24 hours.

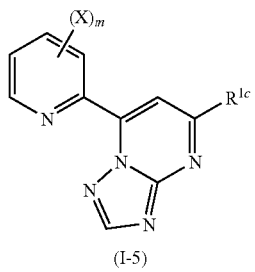

(I-5)

In production process [7], $R^9$, $R^{1c}$, X and m are as defined above.

Production process [7] comprises a first half reaction of reacting the compound of the formula (X) and the compound of the formula (XVI) to obtain the compound of the formula (IX), and a second half reaction of condensing the compound of the formula (IX) and the compound of the formula (V) to obtain the [1,2,4]triazolo[1,5-a]pyrimidine derivative of the formula (I-5).

In the first half reaction in production process [7], the compound of the formula (XVI) may be used in a ratio of from 0.8 to a large excess amount, preferably from 1 to 10 equivalent amount per mol of the compound of the formula (X). This reaction may be carried out in the presence of a base and a solvent. The base may, for example, be the same base as used in the first half reaction in production process [5]. The base may be used in a ratio of from 1 to 5 equivalent amount, preferably from 1 to 2 equivalent amount per mol of the compound of the formula (X). The solvent may be any solvent so long as it is inert to the reaction, and it may, for example, be the same solvent as used in the first half reaction in production process [5], and an ether is preferred. The reaction temperature is usually from 0 to 70° C., preferably from 10 to 50° C. The reaction time is usually from 0.1 to 24 hours.

The second half reaction in production process [7] may be carried out in the same manner as the second half reaction in production process [5].

PRODUCTION PROCESS [9]

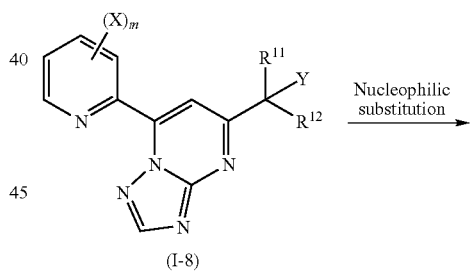

(I-8)

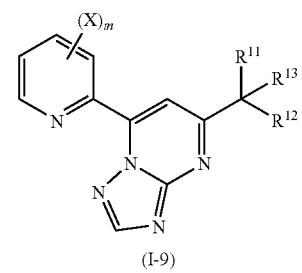

(I-9)

In production process [9], $R^{13}$ is alkyl which may be substituted by A, cycloalkyl which may be substituted by A, alkenyl which may be substituted by A, alkynyl which may be substituted by A, halogen, cyano, aryl, a heterocyclic group which may be substituted by alkyl, $OR^{14}$, $SR^{14}$ or $NR^{15}R^{16}$; each of $R^{14}$, $R^{15}$ and $R^{16}$ which are independent of one another, is alkyl which may be substituted by A, cycloalkyl which may be substituted by A, alkenyl which may be sub-

PRODUCTION PROCESS [8]

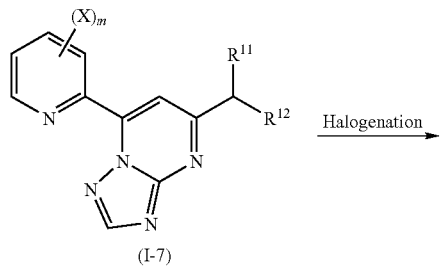

(I-7)

stituted by A or alkynyl which may be substituted by A; and $R^{11}$, $R^{12}$, A, X and m are as defined above.

In production process [9], the compound of the formula (I-8) and a nucleophilic reagent are reacted in the presence of a solvent to produce the [1,2,4]triazolo[1,5-a]pyrimidine derivative of the formula (I-9).

The nucleophilic reagent may, for example, be an alkali metal alkoxide such as sodium methoxide or sodium ethoxide; an alkali metal haloalkoxide such as sodium trifluoromethyl ethoxide; an alkali metal mercaptide such as sodium methyl mercaptane; a primary or secondary amine such as methylamine, dimethylamine, piperidine or morpholine; an organic metal reagent such as methyl magnesium bromide, ethyl magnesium bromide or phenyl magnesium bromide; a fluorinating agent such as potassium fluoride, cesium fluoride or tetrabutylammonium fluoride; or a cyanating agent such as potassium cyanide or sodium cyanide. The nucleophilic reagent may be used in a ratio of from 1 to 5 equivalent amount, preferably from 1 to 3 equivalent amount per mol of the compound of the formula (I-8). The solvent may be any solvent so long as it is inert to the reaction, and it may, for example, be the same solvent as used in the reaction in production process [4]. The reaction temperature is usually from −100 to 50° C., preferably from −70 to 20° C. The reaction time is usually from 6 to 48 hours.

Among the above production processes, production process [1], [5] or [7] is particularly preferred.

Preferred embodiments of pesticides containing the compounds of the present invention will be described below. The pesticides containing the compounds of the present invention are particularly useful, for example, as agents for controlling various pests which become problematic in the agricultural and horticultural fields, i.e. agricultural and horticultural pesticides, or as agents for controlling pests which are parasitic on animals i.e. pesticides against parasites on animals. The agricultural and horticultural pesticides containing the compounds of the present invention are useful as an insecticide, a miticide, a nematicide or a soil pesticide, and they are effective for controlling plant parasitic mites such as two-spotted spider mite (*Tetranychus urticae*), carmine spider mite (*Tetranychus cinnabarinus*), kanzawa spider mite (*Tetranychus kanzawai*), citrus red mite (*Panonychus citri*), European red mite (*Panonychus ulmi*), broad mite (*Polyphagotarsonemus latus*), pink citrus rust mite (*Aculops pelekassi*) and bulb mite (*Rhizoglyphus echinopus*); aphids such as green peach aphid (*Myzus persicae*) and cotton aphid (*Aphis gossypii*); agricultural insect pests such as diamondback moth (*Plutella xylostella*), cabbage armyworm (*Mamestra brassicae*), common cutworm (*Spodoptera litura*), codling moth (*Laspeyresia pomonella*), bollworm (*Heliothis zea*), tobacco budworm (*Heliothis virescens*), gypsy moth (*Lymantria dispar*), rice leafroller (*Cnaphalocrocis medinalis*), *Adoxophyes* sp., colorado potato beetle (*Leptinotarsa decemlineata*), cucurbit leaf beetle (*Aulacophora femoralis*), boll weevil (*Anthonomus grandis*), planthoppers, leafhoppers, scales, bugs, whiteflies, thrips, grasshoppers, anthomyiid flies, scarabs, black cutworm (*Agrotis ipsilon*), cutworm (*Agrotis segetum*) and ants; plant parasitic nematodes such as root-knot nematodes, cyst nematodes, root-lesion nematodes, rice white-tip nematode (*Aphelenchoides besseyi*), strawberry bud nematode (*Nothotylenchus acris*), pine wood nematode (*Bursaphelenchus lignicolus*); gastropods such as slugs and snails; soil pests such as isopods such as pillbugs (*Armadilidium vulgare*) and pillbugs (*Porcellio scaber*); hygienic insect pests such as tropical rat mite (*Ornithonyssus bacoti*), cockroachs, housefly (*Musca domestica*) and house mosquito (*Culex pipiens*); stored grain insect pests such as angoumois grai moth (*Sitotroga cerealella*), adzuki bean weevil (*Callosobruchus chinensis*), red flour beetle (*Tribolium castaneum*) and mealworms; household goods insect pests such as casemaking clothes moth (*Tinea pellionella*), black carpet beetle (*Anthrenus scrophularidae*) and subterranean termites; domestic mites such as mold mite (*Tyrophagus putrescentiae*), *Dermatophagoides farinae*, *Chelacaropsis moorei*, and so on. Among them, the agricultural and horticultural pesticides containing the compounds of the present invention are particularly effective for controlling plant parasitic mites, agricultural insect pests, plant parasitic nematodes or the like. Particularly, they are more effective for controlling plant parasitic mites and agricultural insect pests, and accordingly they are most useful as an insecticide or miticide. Further, they are effective against insect pests having acquired resistance to organophosphorus, carbamate and/or synthetic pyrethroid insecticides. Moreover, the compounds of the present invention have excellent systemic properties, and by the application of the agricultural and horticultural pesticides containing the compounds of the present invention to soil treatment, not only noxious insects, noxious mites, noxious nematodes, noxious gastropods and noxious isopods in soil but also foliage pests can be controlled.

Another preferred embodiments of the pesticides containing compounds of the present invention may be agricultural and horticultural pesticides which collectively control the above-mentioned plant parasitic mites, agricultural insect pests, plant parasitic nematodes, gastropods and soil pests.

The agricultural and horticultural pesticide containing the compound of the present invention, is usually formulated by mixing the compound with various agricultural adjuvants and used in the form of a formulation such as a dust, granules, water-dispersible granules, a wettable powder, a water-based suspension concentrate, an oil-based suspension concentrate, water soluble granules, an emulsifiable concentrate, a soluble concentrate, a paste, an aerosol or an ultra low-volume formulation. However, so long as it is suitable for the purpose of the present invention, it may be formulated into any type of formulation which is commonly used in this field. Such agricultural adjuvants include solid carriers such as diatomaceous earth, slaked lime, calcium carbonate, talc, white carbon, kaoline, bentonite, kaolinite, sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethyl sulfoxide, N,N-dimethylformamide, dimethylacetamide, N-methyl-2-pyrrolidone, and alcohol; anionic surfactants such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyethylene glycol, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins; and so on. Each of the components as such adjuvants may be one or more suitably selected for use, so long as the purpose of the present invention can thereby be accomplished. Further, various additives which are commonly used, such as a filler, a thickener, an anti-settling agent, an antifreezing agent, a dispersion stabilizer, a phytotoxicity reducing agent, an anti-mold agent, and so on, may also be employed.

The weight ratio of the compound of the present invention to the various agricultural adjuvants is usually from 0.001:99.999 to 95:5, preferably from 0.005:99.995 to 90:10.

In the actual application of such a formulation, it may be used as it is, or may be diluted to a predetermined concentration with a diluent such as water, and various spreaders e.g. surfactants, vegetable oils or mineral oils may be added thereto, as the case requires.

The application of the agricultural and horticultural pesticide containing the compound of the present invention can not generally be defined, as it varies depending upon the weather conditions, the type of the formulation, the application season, the application site or the types or degree of outbreak of the pest insects. However, it is usually applied in a concentration of the active ingredient being from 0.05 to 800,000 ppm, preferably from 0.5 to 500,000 ppm, and the dose per unit area is such that the compound of the present invention is from 0.05 to 50,000 g, preferably from 1 to 30,000 g, per hectare. Further, agricultural and horticultural pesticides as another preferred embodiment of pesticides containing the compounds of the present invention may be applied in accordance with the above-described application of pesticides. The present invention includes such a method for controlling pests, particularly for controlling plant parasitic mites, agricultural insect pests or plant parasitic nematodes by such applications.

Various formulations of agricultural and horticultural pesticides containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a food containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

Further, the agricultural and horticultural pesticides containing compounds of the present invention may be mixed with or may be used in combination with other agricultural chemicals, fertilizers or phytotoxicity-reducing agents, whereby synergistic effects or activities may sometimes be obtained. Such other agricultural chemicals include, for example, a herbicide, an insecticide, a miticide, a nematicide, a soil pesticide, a fungicide, an antivirus agent, an attractant, an antibiotic, a plant hormone, a plant growth regulating agent, and so on. Especially, with a mixed pesticide having a compound of the present invention mixed with or used in combination with one or more active compounds of other agricultural chemicals, the application range, the application time, the pesticidal activities, etc. may be improved to preferred directions. The compound of the present invention and the active compounds of other agricultural chemicals may separately be formulated so that they may be mixed for use at the time of application, or they may be formulated together. The present invention includes such a mixed pesticidal composition.

The mixing ratio of the compound of the present invention to the active compounds of other agricultural chemicals can not generally be defined, since it varies depending upon the weather conditions, the types of formulations, the application time, the application site, the types or degree of outbreak of insect pests, etc., but it is usually within a range of from 1:300 to 300:1, preferably from 1:100 to 100:1, by weight. Further, the dose for the application is such that the total amount of the active compounds is from 0.1 to 50,000 g, preferably from 1 to 30,000 g, per hectare. The present invention includes a method for controlling pests by an application of such a mixed pesticide composition.

The active compounds of insect pest control agents such as insecticides, miticides, nematicides or soil pesticides in the above-mentioned other agricultural chemicals, include, for example, (by common names, some of them are still in an application stage, or test codes) organic phosphate compounds such as profenofos, dichlorvos, fenamiphos, fenitrothion, EPN, diazinon, chlorpyrifos, chlorpyrifos-methyl, acephate, prothiofos, fosthiazate, cadusafos, dislufoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlovinphos, chlorfenvinphos, cyanophos, trichlorfon, methidathion, phenthoate, ESP, azinphos-methyl, fenthion, heptenophos, methoxychlor, paration, phosphocarb, demeton-S-methyl, monocrotophos, methamidophos, imicyafos, parathion-methyl, terbufos, phospamidon, phosmet and phorate; carbamate compounds such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC and fenothiocarb; nereistoxin derivatives such as cartap, thiocyclam, bensultap and thiosultap-sodium; organic chlorine compounds such as dicofol, tetradifon, endosulufan, dienochlor and dieldrin; organic metal compounds such as fenbutatin Oxide and cyhexatin; pyrethroid compounds such as fenvalerate, permethrin, cypermethrin, deltamethrin, cyhalothrin, tefluthrin, ethofenprox, flufenprox, cyfluthrin, fenpropathrin, flucythrinate, fluvalinate, cycloprothrin, lambda-cyhalothrin, pyrethrins, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin and phenothrin; benzoylurea compounds such as diflubenzuron, chlorfluazuron, teflubenzuron, flufenoxuron, triflumuron, hexaflumuron, lufenuron, novaluron, noviflumuron, bistrifluoron and fluazuron; juvenile hormone-like compounds such as methoprene, pyriproxyfen, fenoxycarb and diofenolan; pyrazole compounds such as fenpyroximate, fipronil, tebufenpyrad, ethiprole, tolfenpyrad, acetoprole, pyrafluprole and pyriprole; neonicotinoids such as imidacloprid, nitenpyram, acetamiprid, thiacloprid, thiamethoxam, clothianidin, dinotefuran and nithiazine; hydrazine compounds such as tebufenozide, methoxyfenozide, chromafenozide and halofenozide; pyridine compounds such as pyridaryl and flonicamid; tetronic acid compounds such as spirodiclofen; strobilurin compounds such as fluacrypyrim; pyridinamine compounds such as flufenerim; dinitro compounds; organic sulfur compounds; urea compounds; triazine compounds; hydrazone compounds; and other compounds such as buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, spiromesifen, spirotetramat, propargite, clofentezine, metaflumizone, flubendiamide, cyflumetofen, chlorantraniliprole, cyenopyrafen, pyrifluquinazon, fenazaquin, pyridaben, amidoflumet, chlorobenzoate, sulfluramid, hydramethylnon, metaldehyde, HGW 86 and ryanodine. Further, microbial agricultural chemicals such as *Bacillus thuringienses aizawai*, *Bacillus thuringienses kurstaki*, *Bacillus thuringienses israelensis*, *Bacillus thuringienses japonensis*, *Bacillus thuringienses tenebrionis*, insecticidal crystal protein produced by *Bacillus thuringienses*, insect viruses, etomopathogenic fungi, and nematophagous fungi; antibiotics or semisynthetic antibiotics such as avermectin, emamectinbenzoate, milbemectin, milbemycin, spinosad, ivermectin, lepimectin, DE-175, abamectin and emamectin; natural products such as azadirachtin and rotenone; and repellents such as deet may, for example, be mentioned.

The fungicidal active compounds in the above-mentioned other agricultural chemicals include, for example, (by common names, some of them are still in an application stage, or test codes of Japan Plant Protection Association) anilinopyrimidine compounds such as mepanipyrim, pyrimethanil and cyprodinil; pyridinamine compounds such as fluazinam; azole compounds such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole and imibenconazole; quinoxaline compounds such as quinomethionate; dithiocarbamate compounds such as maneb, zineb, mancozeb, polycarbamate, metiram, propineb and thiram; organic chlorine compounds such as fthalide, chlorothalonil and quintozene; imidazole compounds such as benomyl, thiophanate-methyl, carbendazim, thiabendazole, fuberiazole and cyazofamid; cyanoacetamide compounds such as cymoxanil; phenylamide compounds such as metalaxyl, metalaxyl-M, mefenoxam, oxadixyl, ofurace, benalaxyl, benalaxyl-M (another name: kiralaxyl, chiralaxyl), furalaxyl and cyprofuram; sulfenic acid compounds such as dichlofluanid; copper compounds such as cupric hydroxide and oxine copper; isoxazole compounds such as hymexazol; organophosphorus compounds such as fosetyl-Al, tolcofos-methyl, edifenphos, iprobenfos, S-benzyl, O,O-diisopropylphosphorothioate, O-ethyl, S,S-diphenylphosphorodithioate and aluminum ethylhydrogen phosphonate; N-halogenothioalkyl compounds such as captan, captafol and folpet; dicarboximide compounds such as procymidone, iprodione and vinclozolin; benzanilide compounds such as flutolanil, mepronil, zoxamid and tiadinil; anilide compounds such as carboxin, oxycarboxin, thifluzamide, penthiopyrad and boscalid; piperazine compounds such as triforine; pyridine compounds such as pyrifenox; carbinol compounds such as fenarimol and flutriafol; piperidine compounds such as fenpropidine; morpholine compounds such as fenpropimorph, spiroxamine and tridemorph; organotin compounds such as fentin hydroxide and fentin acetate; urea compounds such as pencycuron; cinnamic acid compounds such as dimethomorph and flumorph; phenylcarbamate compounds such as diethofencarb; cyanopyrrole compounds such as fludioxonil and fenpiclonil; strobilurin compounds such as azoxystrobin, kresoxim-methyl, metominofen, trifloxystrobin, picoxystrobin, oryzastrobin, dimoxystrobin, pyraclostrobin, fluoxastrobin and fluacrypyrin; oxazolidinone compounds such as famoxadone; thiazolecarboxamide compounds such as ethaboxam; silylamide compounds such as silthiopham; aminoacid amidecarbamate compounds such as iprovalicarb and benthiavalicarb-isopropyl; imidazolidine compounds such as fenamidone; hydroxanilide compounds such as fenhexamid; benzenesulfonamide compounds such as flusulfamide; oxime ether compounds such as cyflufenamid; phenoxyamide compounds such as fenoxanil; antibiotics such as validamycin, kasugamycin and polyoxins; guanidine compounds such as iminoctadine; and other compounds such as isoprothiolane, Pyroquilon, diclomezine, quinoxyfen, propamocarb hydrochloride, chloropicrin, dazomet, metam-sodium, nicobifen, metrafenone, MTF-753, UBF-307, diclocymet, proquinazid, amisulbrom (another name: amibromdole), pyribencarb, Syngenta 446510 (mandipropamid, dipromandamid), fluopicolide, carpropamid, BCF051, BCM061 and BCM062.

Further, agricultural chemicals which may be used in admixture with or in combination with the compounds of the present invention, may, for example, be the active ingredient compounds in the herbicides as disclosed in Farm Chemicals Handbook (2002 edition), particularly those of soil treatment type.

The pesticides against parasites on animals are effective for controlling e.g. external parasites which are parasitic on the body surface of host animals (such as the back, the axilla, the lower abdomen or inside of the thigh) or internal parasites which are parasitic in the body of host animals (such as the stomach, the intestinal tract, the lung, the heart, the liver, the blood vessels, the subcutis or lymphatic tissues), but they are particularly effective for controlling the external parasites.

The external parasites may, for example, be animal parasitic acarus or fleas. Their species are so many that it is difficult to list all of them, and therefore, their typical examples will be given.

The animal parasitic acarus may, for example, be ticks such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor* reticulates, and *Dermacentor taiwanesis*; common red mite (*Dermanyssus gallinae*); northern fowl mites such as *Ornithonyssus sylviarum*, and *Ornithonyssus bursa*; trombidioids such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi*, and *Helenicula miyagawai;* cheyletidae such as *Cheyletiella yasguri, Cheyletiella parasitivorax*, and *Cheyletiella blakei*; sarcoptic mange mites such as *Psoroptes cuniculi, Chorioptes bovis, Otodectes cynotis, Sarcoptes scabiei*, and *Notoedres cati*; and Demodicidae such as *Demodex canis*. The pesticides against parasites on animals, containing the compounds of the present invention, are particularly effective for the control of ticks among them.

The fleas may, for example, be externally parasitic wingless insects belonging to *Siphonaptera*, more specifically, fleas belonging to *Pulicidae, Ceratephyllus*, etc. Fleas belonging to *Pulicidae* may for example, be *Ctenocephalides canis*, *Ctenocephalides felis*, *Pulex irritans*, *Echidnophaga gallinacea*, *Xenopsylla cheopis*, *Leptopsylla segnis*, *Nosopsyllus fasciatus*, and *Monopsyllus anisus*. The pesticides against parasites on animals, containing the compounds of the present invention, are particularly effective for the control of fleas belonging to *Pulicidae*, particularly *Ctenocephalides canis* and *Ctenocephalides felis*, among them.

Other external parasites may, for example, be sucking lice (*Anoplura*) such as shortnosed cattle louse (*Haematopinus eurysternus*), horse sucking louse (*Haematopinus asini*), sheep louse, longnosed cattle louse (*Linognathus vituli*), and head louse (*Pediculus capitis*); biting lice such as dog biting louse (*Trichodectes canis*); and blood-sucking dipterous insects such as horsefly (*Tabanus trigonus*), biting midges (*Culicoides schultzei*), and blackfly (*Simulium ornatum*). Further, the internal parasites may, for example, be nematodes such as lung worms, whipworms (*Trichuris*), tuberous worms, gastric parasites, ascaris, and filarioidea; cestoda such as *Spirometra erinacei*, *Diphyllobothrium latum*, *Dipylidium caninum*, *Taenia multiceps*, *Echinococcus granulosus*, *Echinococcus multilocularis*; trematoda such as *Schistosoma japonicum*, *Fasciola hepatica*; and protozoa such as coccidia, malaria parasites (*Plasmodium malariae*), intestinal sarcocyst, toxoplasma, and cryptosporidium.

The host animals may, for example, be pet animals, domestic animals, and poultry, such as dogs, cats, mice, rats, hamsters, guinea pigs, squirrels, rabbits, ferrets, birds (such as pigeons, parrots, hill mynas, Java sparrows, honey parrots, lovebirds and canaries), cows, horses, pigs, sheep, ducks and chickens. The pesticides against parasites on animals, containing the compounds of the present invention, are particularly effective for the control of pests parasitic on pet animals or domestic animals, especially for the control of external parasites, among them. Among pet animals or domestic animals, they are effective particularly for dogs and cats, cows and horses.

When the compound of the present invention is used as a pesticide against parasites on animals, it may be used as it is or may be used together with suitable adjuvants, as formulated into various formulations such as a dust, granules, tablets, a powder, capsules, a soluble concentrate, an emulsifiable concentrate, a water-based suspension concentrate and an oil-based suspension concentrate. In addition to such formulations, it may be formulated into any type of formulation which is commonly used in this field, so long as it is suitable for the purpose of the present invention. The adjuvants to be used for formulations may, for example, be anionic surfactants or nonionic surfactants exemplified above as adjuvants for formulation of agricultural and horticultural pesticides; a cationic surfactant such as cetyl trimethylammonium bromide; a solvent such as water, acetone, acetonitrile, monomethylacetamide, dimethylacetamide, dimethylformamide, 2-pyrrolidone, N-methyl-2-pyrrolidone, kerosene, triacetin, methanol, ethanol, isopropanol, benzyl alcohol, ethylene glycol, propylene glycol, polyethylene glycol, liquid polyoxyethylene glycol, butyl diglycol, ethylene glycol monomethyl ether, ethylene glycol monoethyl ether, diethylene glycol monoethyl ether, diethylene glycol n-butyl ether, dipropylene glycol monomethyl ether, or dipropylene glycol n-butyl ether; an antioxidant such as butylhydroxyanisole, butylhydroxytoluene, ascorbic acid, sodium hydrogenmetasulfite, propyl gallate or sodium thiosulfate; a coating film-forming agent such as polyvinylpyrrolidone, polyvinyl alcohol, or a copolymer of vinyl acetate and vinyl pyrrolidone; the vegetable oils and mineral oils as exemplified above as adjuvants for formulation of agricultural and horticultural pesticides; a carrier such as lactose, sucrose, glucose, starch, wheat flour, corn powder, soybean cake and meal, defatted rice bran, calcium carbonate or other commercially available feed materials; and so on. One or more of the respective components of these adjuvants may be suitably selected for use, so long as such will not depart from the purpose of the present invention. Further, other than the above-mentioned adjuvants, some among those known in this field may suitably be selected for use, and still further, some among the above-mentioned various adjuvants to be used in the agricultural and horticultural field may suitably be selected for use.

The blend ratio of the compound of the present invention to various adjuvants is usually from 0.1:99.9 to 90:10. In the actual use of such a formulation, it may be used as it is, or may be diluted to a predetermined concentration with a diluent such as water, and various spreaders (e.g. surfactants, vegetable oils or mineral oils) may be added thereto, as the case requires.

Administration of the compound of the present invention to a host animal is carried out orally or parenterally. As an oral administration method, a method of administering a tablet, a liquid agent, a capsule, a wafer, a biscuit, a minced meat or other feed, containing the compound of the present invention, may be mentioned. As a parenteral administration method, there may, for example, be mentioned a method wherein the compound of the present invention is formulated into a suitable formulation and then taken into the body by e.g. intravenous administration, intramuscular administration, intradermal administration, hypodermic administration, etc.; a method wherein it is administered on the body surface by spot-on treatment, pour-on treatment or spray treatment; or a method of embedding a resin fragment or the like containing the compound of the present invention under the skin of the host animal.

The dose of the compound of the present invention to a host animal varies depending upon the administration method, the purpose of administration, the deceased symptom, etc., but it is usually administered in a proportion of from 0.01 mg to 100 g, preferably from 0.1 mg to 10 g, per 1 kg of the body weight of the host animal.

The present invention also includes a method for controlling a pest by the above-mentioned administration method or by the above-mentioned dose, particularly a method for controlling external parasites or internal parasites.

Further, in the present invention, by controlling pests parasitic on animals as described above, it is possible to prevent or cure various diseases of the host animal thereby caused in some cases. Thus, the present invention also includes a preventive or therapeutic agent for an animal disease caused by parasites, containing the compound of the present invention as an active ingredient, and a method for preventing or curing an animal disease caused by parasites.

When the compound of the present invention is used as a pesticide against parasites on animals, various vitamins, minerals, amino acids, nutrients, enzymes, antipyretics, sedatives, antiphlogistics, fungicides, colorants, aromatic substances, preservatives, etc., may be used in admixture with or in combination with the adjuvants. Further, as the case requires, other animal drugs or agricultural chemicals, such as vermicides, anti-coccidium agents, insecticides, miticides, pulicides, nematocides, bactericides or antibacterial agents, may be mixed or combined for use, whereby improved effects may sometimes be obtained. The present invention includes such a mixed pesticidal composition having the above-mentioned various components mixed or combined for use, and further a method for controlling a pest by using it, particularly a method for controlling external parasites or internal parasites.

Preferred embodiments of the compounds of the above formula (I) are as follows. However, it should be understood that the present invention is by no means thereby restricted.

(1) A pyridyl-triazolopyrimidine derivative represented by the above formula (I) or its salt.

(2) The pyridyl-triazolopyrimidine derivative or its salt as defined in the above (1), wherein $R^1$ is hydrogen, alkyl which may be substituted by A, cycloalkyl which may be substituted by A, alkenyl which may be substituted by A, alkynyl which may be substituted by A, halogen, cyano, aryl, a heterocyclic group, $OR^2$, $S(O)_nR^3$ or $NR^4R^5$; $R^2$ is hydrogen, alkyl, alkenyl, alkynyl, haloalkyl or aryl; $R^3$ is alkyl; $R^5$ is hydrogen or alkyl; A is halogen, $OR^2$, $S(O)_nR^3$, $NR^4R^5$, cyano, cycloalkyl, aryl or a heterocyclic group; and X is alkyl, alkenyl, alkynyl, halogen, haloalkyl, cyano or nitro.

(3) The pyridyl-triazolopyrimidine derivative or its salt as defined in the above (2), wherein $R^1$ is hydrogen, alkyl, haloalkyl, cycloalkyl, alkenyl, alkynyl, halogen, cyano, aryl, a heterocyclic group, $OR^2$, $S(O)_nR^3$ or $NR^4R^5$.

(4) The pyridyl-triazolopyrimidine derivative or its salt as defined in the above (3), wherein $R^1$ is hydrogen, alkyl, haloalkyl, alkynyl, cyano, aryl, a heterocyclic group, $OR^2$, $S(O)_nR^3$ or $NR^4R^5$.

(5) The pyridyl-triazolopyrimidine derivative or its salt as defined in the above (2), wherein $R^1$ is alkyl which may be substituted by A, cycloalkyl which may be substituted by A, alkenyl which may be substituted by A, alkynyl which may be substituted by A, halogen, cyano, aryl, a heterocyclic group, $OR^2$, $S(O)_nR^3$ or $NR^4R^5$.

(6) The pyridyl-triazolopyrimidine derivative or its salt as defined in the above (5), wherein $R^1$ is alkyl, haloalkyl, cycloalkyl, alkenyl, alkynyl, cyano, aryl, a heterocyclic group, $OR^2$, $S(O)_nR^3$ or $NR^4R^5$.

(7) The pyridyl-triazolopyrimidine derivative or its salt as defined in the above (6), wherein $R^1$ is alkyl, haloalkyl, cycloalkyl or alkenyl.

(8) The pyridyl-triazolopyrimidine derivative or its salt as defined in the above (5), wherein $R^1$ is alkyl, haloalkyl, alkynyl, cyano, aryl, a heterocyclic group, $OR^2$, $S(O)_nR^3$ or $NR^4R^5$.

(9) The pyridyl-triazolopyrimidine derivative or its salt as defined in the above (8), wherein $R^1$ is alkyl, haloalkyl, alkynyl, cyano, aryl, $OR^2$, $S(O)_nR^3$ or $NR^4R^5$.

(10) The pyridyl-triazolopyrimidine derivative or its salt as defined in the above (9), wherein $R^1$ is alkyl, trifluoromethyl, alkynyl, cyano, phenyl, alkoxy, alkylthio, alkylsulfonyl, dialkylamino or amino.

(11) The pyridyl-triazolopyrimidine derivative or its salt as defined in the above (2), wherein X is alkyl, alkynyl, halogen, haloalkyl, cyano or nitro.

EXAMPLES

Now, the present invention will be described in further detail with reference to Examples, but it should be understood that the present invention is by no means restricted thereto. Firstly, Preparation Examples of the compound of the present invention will be described.

Preparation Example 1

Preparation of 7-(3-bromo-5-(trifluoromethyl)pyridin-2-yl)-[1,2,4]triazolo[1,5-a]pyrimidine (compound No. 4)

(1) 728 mg of 2-acetyl-3-bromo-5-(trifluoromethyl)pyridine and 466 mg of N,N-dimethylformamide dimethyl acetal were reacted in 5 mL of toluene at 100° C. for 16 hours. The reaction liquid was concentrated under reduced pressure to obtain 866 mg of 1-(3-bromo-5-(trifluoromethyl)pyridin-2-yl)-3-(dimethylamino)-2-propen-1-one (after-mentioned intermediate No. IV-7).

(2) 866 mg of 1-(3-bromo-5-(trifluoromethyl)pyridin-2-yl)-3-(dimethylamino)-2-propen-1-one obtained in (1) was dissolved in 10 mL of acetic acid, and 225 mg of 3-amino-1H-1,2,4-triazole was added, followed by reflux with heating for 7 hours. After completion of the reaction, water was added to the reaction liquid, followed by extraction with ethyl acetate, the organic layer was washed with water and dried over anhydrous magnesium sulfate, and the solvent was distilled off under reduced pressure. The residue was purified by silica gel column chromatography (eluent: n-hexane/ethyl acetate=1/2) to obtain 402 mg of the desired product.

Preparation Example 2

Preparation of 7-(3-chloro-5-(trifluoromethyl)pyridin-2-yl)-5-methyl-[1,2,4]triazolo[1,5-a]pyrimidine (compound No. 19)

(1) 1.0 g of 2-acetyl-3-chloro-5-(trifluoromethyl)pyridine and 715 mg of N,N-dimethylacetamide dimethyl acetal were reacted in 6 mL of toluene at 100° C. for 14 hours. The reaction liquid was concentrated under reduced pressure, and the obtained residue was purified by silica gel column chromatography (eluent: ethyl acetate) to obtain 869 mg of 1-(3-chloro-5-(trifluoromethyl)pyridin-2-yl)-3-(dimethylamino)-2-buten-1-one (after-mentioned intermediate No. IV-1).

(2) 850 mg of 1-(3-chloro-5-(trifluoromethyl)pyridin-2-yl)-3-(dimethylamino)-2-buten-1-one obtained in (1) was dissolved in 3 mL of acetic acid, and 244 mg of 3-amino-1H-1,2,4-triazole was added, followed by reflux with heating for 17 hours. After completion of the reaction, water was added to the reaction liquid, followed by extraction with ethyl acetate, the organic layer was washed with a saturated sodium hydrogen carbonate aqueous solution and dried over anhydrous sodium sulfate, and the solvent was distilled off under reduced pressure. The residue was purified by silica gel column chromatography (eluent: n-hexane/ethyl acetate=1/1) to obtain 609 mg of the desired product.

Preparation Example 3

Preparation of 7-(3-chloro-5-(trifluoromethyl)pyridin-2-yl)5-(trifluoromethyl)-[1,2,4]triazolo[1,5-a]pyrimidine (compound No. 20)

(1) 608 mg of a sodium ethoxide 21% ethanol solution was added at 0° C. to a tetrahydrofuran (dehydrated) 9 mL solution of 1 g of 2-acetyl-3-chloro-5-(trifluoromethyl)pyridine and 635 mg of ethyl 2,2,2-trifluoroacetate, followed by stirring at room temperature for 13 hours. After completion of the reaction, water was added to the reaction liquid, followed by extraction with ethyl acetate, the organic layer was dried over anhydrous sodium sulfate, and the solvent was distilled off under reduced pressure to obtain 1.4 g of 1-(3-chloro-5-(trifluoromethyl)pyridin-2-yl)-4,4,4-trifluorobutan-1,3-dione (after-mentioned intermediate No. IX-25).

(2) To an acetic acid 9 mL solution of 1-(3-chloro-5-(trifluoromethyl)pyridin-2-yl)-4,4,4-trifluorobutan-1,3-dione obtained in (1), 376 mg of 3-amino-1H-1,2,4-triazole was added, followed by reflux with heating for 6 hours. After completion of the reaction, the solvent was distilled off under reduced pressure. The residue was purified by silica gel column chromatography (eluent: n-hexane/ethyl acetate=4/1) to obtain 111 mg of the desired product.

Preparation Example 4

Preparation of 5-(methylthio)-7-(5-(trifluoromethyl) pyridin-2-yl)-[1,2,4]triazolo[1,5-a]pyrimidine (compound No. 21)

(1) 3.68 g of potassium t-butoxide and 3.1 g of 2-acetyl-5-(trifluoromethyl)pyridine were added to 55 mL of tetrahydrofuran (dehydrated), followed by stirring at room temperature. 10 Minutes later, 1.37 g of carbon disulfide and 4.9 g of methyl iodide were added in this order, followed by stirring at room temperature for 12 hours. After completion of the reaction, water was added to the reaction liquid, followed by extraction with ethyl acetate, the organic layer was dried over anhydrous sodium sulfate, and the solvent was distilled off under reduced pressure. The residue was purified by silica gel column chromatography (eluent: n-hexane/ethyl acetate=9/1) to obtain 3.0 g of 3,3-bis(methylthio)-1-(5-(trifluoromethyl)pyridin-2-yl)-2-propen-1-one.

(2) To a N-methylpyrrolidinone 30 mL solution of 2.7 g of 3,3-bis(methylthio)-1-(5-(trifluoromethyl)pyridin-2-yl)-2-propen-1-one obtained in (1), 1.16 g of 3-amino-1H-1,2,4-triazole and 2.5 g of potassium carbonate were added, followed by stirring at 150° C. for 30 minutes. After completion of the reaction, the reaction liquid was returned to room temperature, water was added to the reaction liquid, followed by extraction with ethyl acetate, the organic layer was washed with a saturated salt solution and dried over anhydrous sodium sulfate, and the solvent was distilled off under reduced pressure. The residue was purified by silica gel column chromatography (eluent: n-hexane/ethyl acetate=4/1) to obtain 600 mg of the desired product.

Preparation Example 5

Preparation of 5-(methylsulfonyl)-7-(5-(trifluoromethyl)pyridin-2-yl)-[1,2,4]triazolo[1,5-a]pyrimidine (compound No. 22)

700 mg of m-chloroperbenzoic acid was added to a chloroform 120 mL solution of 420 mg of 5-(methylthio)-7-(5-(trifluoromethyl)pyridin-2-yl)-[1,2,4]triazolo[1,5-a]pyrimidine, followed by reflux with heating for 2 hours. After completion of the reaction, the reaction liquid was returned to room temperature, a 1N sodium hydroxide aqueous solution was added to the reaction liquid, followed by extraction with chloroform, the organic layer was dried over anhydrous sodium sulfate, and the solvent was distilled off under reduced pressure. The residue was purified by silica gel column chromatography (eluent: n-hexane/ethyl acetate=1/1) to obtain 420 mg of the desired product.

Preparation Example 6

Preparation of 5-methoxy-7-(5-(trifluoromethyl) pyridin-2-yl)-[1,2,4]triazolo[1,5-a]pyrimidine (compound No. 25)

62 mg of a sodium methoxide 28% methanol solution was added to a methanol 3 mL solution of 100 mg of 5-(methylsulfonyl)-7-(5-(trifluoromethyl)pyridin-2-yl)-[1,2,4]triazolo[1,5-a]pyrimidine, followed by stirring at room temperature for 5 minutes. After completion of the reaction, water was added to the reaction liquid, followed by extraction with ethyl acetate, the organic layer was dried over anhydrous sodium sulfate, and the solvent was distilled off under reduced pressure. The residue was purified by silica gel column chromatography (eluent: n-hexane/ethyl acetate=1/1) to obtain 85 mg of the desired product.

Preparation Example 7

Preparation of 5-phenyl-7-(5-(trifluoromethyl)pyridin-2-yl)-[1,2,4]triazolo[1,5-a]pyrimidine (compound No. 28)

0.2 mL of a phenyl magnesium bromide 3.0 M tetrahydrofuran solution was added at 0° C. to a tetrahydrofuran (dehydrated) 3 mL solution of 200 mg of 5-(methylsulfonyl)-7-(5-(trifluoromethyl)pyridin-2-yl)-[1,2,4]triazolo[1,5-a]pyrimidine, followed by stirring at 0° C. for 5 minutes. After completion of the reaction, water was added to the reaction liquid, followed by extraction with ethyl acetate, the organic layer was dried over anhydrous sodium sulfate, and the solvent was distilled off under reduced pressure. The residue was purified by silica gel column chromatography (eluent: n-hexane/ethyl acetate=4/1) to obtain 93 mg of the desired product.

Preparation Example 8

Preparation of 7-(3-chloro-5-(trifluoromethyl)pyridin-2-yl)-5-cyclopropyl-[1,2,4]triazolo[1,5-a]pyrimidine (compound No. 82)

(1) 805 mg of sodium ethoxide was added to a solution having 2 g of ethyl-3-chloro-5-(trifluoromethyl)pyridine-2-carboxylate and 3.4 g of cyclopropyl methyl ketone dissolved in 15 mL of tetrahydrofuran (dehydrated), followed by stirring at room temperature for 10 minutes. After completion of the reaction, 1N hydrochloric acid was added to the reaction liquid to make it acidic, followed by extraction with ethyl acetate, the organic layer was dried over anhydrous sodium sulfate, and the solvent was distilled off under reduced pressure to obtain a liquid material, which was confirmed to contain 1-(3-chloro-5-(trifluoromethyl)pyridin-2-yl)-cyclopropylpropan-1,3-dione (intermediate No. IX-18) by $^1$H-NMR.

(2) To the entire liquid material obtained in (1), 15 mL of acetic acid and 730 mg of 3-amino-1H-1,2,4-triazole were added, followed by stirring at 100° C. overnight. After completion of the reaction, the solvent was distilled off under reduced pressure, and water was added to the obtained residue, followed by extraction with ethyl acetate. The organic layer was washed with a saturated sodium hydrogen carbonate aqueous solution and dried over anhydrous sodium sulfate, and the solvent was distilled off under reduced pressure. The residue was purified by silica gel column chromatography (eluent: n-hexane/ethyl acetate=4/1) to obtain 1.67 g of the desired product.

Preparation Example 9

Preparation of 7-(3-bromo-5-(trifluoromethyl)pyridin-2-yl)-5-isopropyl-[1,2,4]triazolo[1,5-a]pyrimidine (compound No. 95)

(1) 408 mg of sodium ethoxide was added to a solution having 1.2 g of ethyl-3-bromo-5-(trifluoromethyl)pyridine-2-carboxylate and 1.73 g of isopropyl methyl ketone dissolved in 13 mL of tetrahydrofuran (dehydrated), followed by stirring at room temperature for 15 minutes. After completion of the reaction, 1N hydrochloric acid was added to the reaction liquid to make it acidic, followed by extraction with ethyl acetate, the organic layer was dried over anhydrous sodium sulfate, and the solvent was distilled off under reduced pressure to obtain a liquid containing 1-(3-bromo-5-(trifluoromethyl)pyridin-2-yl)-4-methylpentan-1,3-dione (intermediate No. IX-22).

(2) To the entire liquid obtained in (1), 8 mL of acetic acid and 370 mg of 3-amino-1H-1,2,4-triazole were added, followed by stirring at 100° C. overnight. After completion of the reaction, the solvent was distilled off under reduced pressure, and water was added to the obtained residue, followed by extraction with ethyl acetate. The organic layer was washed with a saturated sodium hydrogen carbonate aqueous solution and dried over anhydrous sodium sulfate, and the solvent was distilled off under reduced pressure. The residue was purified by silica gel column chromatography (eluent: n-hexane/ethyl acetate=3/1) to obtain 650 mg of the desired product.

Preparation Example 10

Preparation of 7-(3-chloro-5-(trifluoromethyl)pyridin-2-yl)-5-ethyl-[1,2,4]triazolo[1,5-a]pyrimidine (compound No. 16)

(1) 3.2 g of sodium ethoxide was added to a solution having 6.0 g of ethyl-3-chloro-5-(trifluoromethyl)pyridine-2-carboxylate and 2.6 g of methyl ethyl ketone dissolved in 80 mL of tetrahydrofuran (dehydrated), followed by stirring at room temperature for 15 minutes. After completion of the reaction, 1N hydrochloric acid was added to the reaction liquid to make it acidic, followed by extraction with ethyl acetate, the organic layer was dried over anhydrous sodium sulfate, and the solvent was distilled off under reduced pressure to obtain a liquid material, which was confirmed to contain 1-(3-chloro-5-(trifluoromethyl)pyridin-2-yl)-pentan-1,3-dione (intermediate No. IX-7) by $^1$H-NMR.

(2) To the entire liquid material obtained in (1), 65 mL of acetic acid and 2.2 g of 3-amino-1H-1,2,4-triazole were added, followed by stirring at 100° C. overnight. After completion of the reaction, the solvent was distilled off under reduced pressure, and water was added to the obtained residue, followed by extraction with ethyl acetate. The organic layer was washed with a saturated sodium hydrogen carbonate aqueous solution and dried over anhydrous sodium sulfate, and the solvent was distilled off under reduced pressure. The residue was purified by silica gel column chromatography (eluent: n-hexane/ethyl acetate=3/1) to obtain 3.1 g of the desired product.

Preparation Example 11

Preparation of 5-(1-bromoethyl)-7-(3-chloro-5-(trifluoromethyl)pyridin-2-yl)-[1,2,4]triazolo[1,5-a]pyrimidine (compound No. 101)

4.47 g of N-bromosuccinimide and 50 mg of azobisisobutylonitrile (AIBN) were added to a solution having 5.76 g of 7-(3-chloro-5-(trifluoromethyl)pyridin-2-yl)-5-ethyl-[1,2,4]triazolo[1,5-a]pyrimidine dissolved in 30 mL of chloroform, followed by stirring overnight under reflux with heating. After completion of the reaction, water was added to the reaction liquid, followed by extraction with ethyl acetate, the organic layer was dried over anhydrous sodium sulfate, and the solvent was distilled off under reduced pressure. The residue was purified by silica gel column chromatography (eluent: n-hexane/ethyl acetate=5/2) to obtain 4.47 g of the desired product as a solid.

Preparation Example 12

Preparation of 5-bromomethyl-7-(3-chloro-5-(trifluoromethyl)pyridin-2-yl)-[1,2,4]triazolo[1,5-a]pyrimidine (compound No. 60)

312 mg of N-bromosuccinimide and 13 mg of azobisisobutylonitrile (AIBN) were added to a solution having 500 mg of 7-(3-chloro-5-(trifluoromethyl)pyridin-2-yl)-5-methyl-[1,2,4]triazolo[1,5-a]pyrimidine dissolved in 3 mL of carbon tetrachloride, followed by stirring overnight under reflux with heating. After completion of the reaction, water was added to the reaction liquid, followed by extraction with ethyl acetate, the organic layer was dried over anhydrous sodium sulfate, and the solvent was distilled off under reduced pressure. The residue was purified by silica gel column chromatography (eluent: n-hexane/ethyl acetate=7/3) to obtain 86 mg of the desired product.

Preparation Example 13

Preparation of 7-(3-chloro-5-(trifluoromethyl)pyridin-2-yl)-5-((2,2,2-trifluoroethoxy)methyl)-[1,2,4]triazolo[1,5-a]pyrimidine (compound No. 63)

230 mg of 2,2,2-trifluoroethanol was added to a tetrahydrofuran (dehydrated) 8 mL solution of 33 mg of 60% sodium hydride, followed by stirring for 5 minutes, and 300 mg of 5-bromomethyl-7-(3-chloro-5-(trifluoromethyl)pyridin-2-yl)-[1,2,4]triazolo[1,5-a]pyrimidine was added at room temperature, followed by stirring for 5 minutes. After completion of the reaction, 1N hydrochloric acid was added to make it acidic, followed by extraction with ethyl acetate, the organic layer was dried over anhydrous sodium sulfate, and the solvent was distilled off under reduced pressure. The residue was purified by silica gel column chromatography (eluent: n-hexane/ethyl acetate=1/1) to obtain 97 mg of the desired product.

Typical examples of the compound of the above formula (I) will be given in Table 1. These compounds can be prepared by the above-described Preparation Examples or by the above-mentioned various processes for the production of the compound of the present invention. In Table 1, No. represents the compound No., Me methyl, Et ethyl, n-Pr normal propyl, i-Pr isopropyl, n-Bu normal butyl, t-Bu tertiary butyl, sec-Bu secondary butyl, Ac acetyl, and Ph phenyl, respectively, and the temperature shown as the physical properties is the melting point. Further, $^1$H-NMR data of some of the compounds of the above formula (I) are shown in Table 2.

Typical examples of the compound of the above formula (IV) in production process [1] will be given in Table 3. These compounds can be prepared by the above-described Preparation Examples or by the above-described various production processes. In Table 3, No. represents the intermediate No., Me methyl, Et ethyl, and n-Pr normal propyl, respectively, and the temperature shown as the physical properties is the melting point. Further, $^1$H-NMR data of some of the compounds of the above formula (IV) are shown in Table 4.

Typical examples of the compounds of the formula (IX) in production processes [5] and [7] will be given in Table 5. These compounds can be prepared by the above-described Preparation Examples or by the above-described various production processes. In Table 5, No. represents the intermediate No., Me methyl, Et ethyl, i-Pr isopropyl, i-Bu isobutyl, t-Bu tertiary butyl, sec-Bu secondary butyl and Ph phenyl, respectively, and the temperature shown as the physical properties is the melting point. Further, $^1$H-NMR data of some of the compounds of the above formula (IX) are shown in Table 6.

TABLE 1

| No. | R$^1$ | X$^1$ | X$^2$ | X$^3$ | X$^4$ | Physical properties |
|---|---|---|---|---|---|---|
| 1 | H | CF$_3$ | H | H | H | 118 to 120° C. |
| 2 | H | H | CF$_3$ | H | H | 110 to 112° C. |
| 3 | H | H | H | H | CF$_3$ | 173 to 174° C. |
| 4 | H | H | CF$_3$ | H | Br | oil |
| 5 | H | H | CF$_3$ | H | F | oil |
| 6 | H | H | Cl | H | Cl | 134 to 136° C. |
| 7 | H | H | CF$_3$ | H | C≡C-t-Bu | oil |
| 8 | H | H | H | CF$_3$ | H | 168° C. |
| 9 | H | Cl | H | CF$_3$ | H | 183 to 185° C. |
| 10 | H | Cl | Cl | CF$_3$ | Cl | 132° C. |
| 11 | H | H | NO$_2$ | H | Cl | 57 to 60° C. |
| 12 | H | H | CF$_3$ | H | NO$_2$ | oil |
| 13 | H | H | Me | H | Cl | oil |
| 14 | H | H | CF$_3$ | H | CN | oil |
| 15 | Me | H | CF$_3$ | H | Br | 156 to 158° C. |
| 16 | Et | H | CF$_3$ | H | Cl | oil |
| 17 | n-Pr | H | CF$_3$ | H | Cl | oil |
| 18 | Me | H | CF$_3$ | H | H | solid |
| 19 | Me | H | CF$_3$ | H | Cl | 105 to 107° C. |
| 20 | CF$_3$ | H | CF$_3$ | H | Cl | oil |
| 21 | SMe | H | CF$_3$ | H | H | 177 to 179° C. |
| 22 | SO$_2$Me | H | CF$_3$ | H | H | At least 300° C. |
| 23 | NMe$_2$ | H | CF$_3$ | H | H | 195 to 198° C. |
| 24 | Me | H | H | H | CF$_3$ | 167 to 169° C. |
| 25 | OMe | H | CF$_3$ | H | H | 255° C. |
| 26 | OCH$_2$C≡CCH$_3$ | H | CF$_3$ | H | H | 168 to 170° C. |
| 27 | CN | H | CF$_3$ | H | H | 175° C. |
| 28 | Ph | H | CF$_3$ | H | H | 185 to 187° C. |
| 29 | NH$_2$ | H | CF$_3$ | H | H | 201 to 203° C. |
| 30 | i-Pr | H | CF$_3$ | H | H |  |
| 31 | t-Bu | H | CF$_3$ | H | H |  |
| 32 | CH=CHMe | H | CF$_3$ | H | H | 198 to 201° C. |
| 33 | C≡CMe | H | CF$_3$ | H | H | 120 to 123° C. |
| 34 | cyclopropyl | H | CF$_3$ | H | H |  |
| 35 | cyclopentyl | H | CF$_3$ | H | H |  |
| 36 | cyclohexyl | H | CF$_3$ | H | H |  |
| 37 | 2-thienyl | H | CF$_3$ | H | H |  |
| 38 | OCH$_2$—CF$_3$ | H | CF$_3$ | H | H | 160 to 162° C. |
| 39 | CH$_2$CN | H | CF$_3$ | H | H |  |
| 40 | F | H | CF$_3$ | H | H |  |
| 41 | Me | H | CF$_3$ | H | I | 186 to 189° C. |
| 42 | Me | H | CF$_3$ | H | F |  |
| 43 | Me | H | CF$_3$ | H | CN | oil |
| 44 | Me | H | CF$_3$ | H | Me | 123° C. |

TABLE 1-continued

| No. | R¹ | X¹ | X² | X³ | X⁴ | Physical properties |
|-----|-----|-----|-----|-----|-----|-----|
| 45 | F | H | CF₃ | H | Cl | |
| 46 | Cl | H | CF₃ | H | Cl | |
| 47 | Br | H | CF₃ | H | Cl | |
| 48 | CH₂OMe | H | CF₃ | H | Cl | oil |
| 49 | CH₂OPh | H | CF₃ | H | Cl | |
| 50 | CH₂Ph | H | CF₃ | H | Cl | |
| 51 | Me | CF₃ | H | CF₃ | H | 113° C. |
| 52 | Me | H | CF₃ | H | Ph | oil |
| 53 | CH₂Cl | H | CF₃ | H | Cl | oil |
| 54 | CHCl₂ | H | CF₃ | H | Cl | oil |
| 55 | Me | H | CF₃ | H | COOEt | 95 to 98° C. |
| 56 | Me | H | CF₃ | H | COOH | 229 to 231° C. |
| 57 | Me | H | Cl | H | CF₃ | |
| 58 | Me | H | CF₃ | H | COMe | oil |
| 59 | Me | CF₃ | H | H | CF₃ | 150 to 151° C. |
| 60 | CH₂Br | H | CF₃ | H | Cl | oil |
| 61 | CHBr₂ | H | CF₃ | H | Cl | 147 to 150° C. |
| 62 | CH₂OCH₂CH₂OMe | H | CF₃ | H | Cl | oil |
| 63 | CH₂OCH₂CF₃ | H | CF₃ | H | Cl | oil |
| 64 | CH₂OCH(CF₃)₂ | H | CF₃ | H | Cl | 140 to 143° C. |
| 65 | CH₂NMe₂ | H | CF₃ | H | Cl | oil |
| 66 | CH₂NMeCH₂CH₂OH | H | CF₃ | H | Cl | oil |
| 67 | Me | Cl | CF₃ | H | CF₃ | oil |
| 68 | Me | Cl | CF₃ | H | Cl | 142 to 143° C. |
| 69 | Me | CF₃ | H | H | Cl | |
| 70 | CN | H | CF₃ | H | Cl | 164 to 166° C. |
| 71 | Me | CF₃ | H | H | Br | |
| 72 | CH₂SCH₂COOMe | H | CF₃ | H | Cl | oil |
| 73 | CH₂CN | H | CF₃ | H | Cl | oil |
| 74 | CH₂NMeCH₂CH₂OMe | H | CF₃ | H | Cl | oil |
| 75 | CH₂NMeCH₂CN | H | CF₃ | H | Cl | oil |
| 76 | CH₂-morpholinyl | H | CF₃ | H | Cl | oil |
| 77 | CH₂CH(CN)₂ | H | CF₃ | H | Cl | oil |
| 78 | Me | H | CF₃ | H | NO₂ | oil |
| 79 | Me | H | CF₃ | H | Et | oil |
| 80 | i-Pr | H | CF₃ | H | Cl | 86 to 88° C. |
| 81 | CH₂(i-Pr) | H | CF₃ | H | Cl | oil |
| 82 | cyclopropyl | H | CF₃ | H | Cl | 93 to 95° C. |
| 83 | n-Bu | H | CF₃ | H | Cl | oil |
| 84 | 1-methylpyrrol-2-yl | H | CF₃ | H | Cl | 189 to 190° C. |
| 85 | Ph | H | CF₃ | H | Cl | 218 to 220° C. |
| 86 | CH₂CH₂(i-Pr) | H | CF₃ | H | Cl | 90 to 92° C. |
| 87 | sec-Bu | H | CF₃ | H | Cl | oil |
| 88 | thiazol-2-yl | H | CF₃ | H | Cl | 187 to 189° C. |

TABLE 1-continued

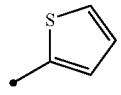

| No. | R¹ | X¹ | X² | X³ | X⁴ | Physical properties |
|---|---|---|---|---|---|---|
| 89 | t-Bu | H | CF₃ | H | Cl | oil |
| 90 | 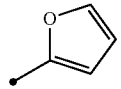 | H | CF₃ | H | Cl | solid |
| 91 | 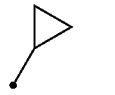 | H | CF₃ | H | Cl | 196 to 198° C. |
| 92 | 2-pyridyl | H | CF₃ | H | Cl | 183 to 186° C. |
| 93 | 4-pyridyl | H | CF₃ | H | Cl | 213° C. |
| 94 | 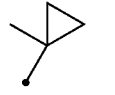 | H | CF₃ | H | Br | 139 to 141° C. |
| 95 | i-Pr | H | CF₃ | H | Br | 105 to 108° C. |
| 96 | Me | CF₃ | Cl | H | H | 208 to 211° C. |
| 97 | Me | CF₃ | Br | H | H | 222 to 226° C. |
| 98 | 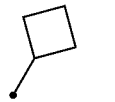 | H | CF₃ | H | Cl | 174 to 178° C. |
| 99 | 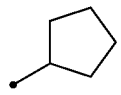 | H | CF₃ | H | Cl | oil |
| 100 | CHMeOH | H | CF₃ | H | Cl | 178° C. |
| 101 | CHMeBr | H | CF₃ | H | Cl | 118° C. |
| 102 | CHMeNHMe | H | CF₃ | H | Cl | amorphous |
| 103 | CHMeF | H | CF₃ | H | Br | |
| 104 | CHMeF | H | CF₃ | H | Cl | oil |
| 105 | Me | Cl | CF₃ | H | F | viscous oil |
| 106 | Me | NMe₂ | CF₃ | H | Cl | 149 to 150° C. |
| 107 | 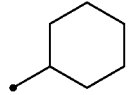 | H | CF₃ | H | Cl | oil |
| 108 | 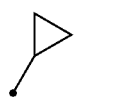 | H | CF₃ | H | Cl | 111 to 113° C. |
| 109 | CH₂(t-Bu) | H | CF₃ | H | Cl | 155 to 158° C. |
| 110 | 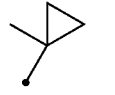 | H | CF₃ | H | COOEt | oil |
| 111 | CHMeOAc | H | CF₃ | H | Cl | 98 to 99° C. |
| 112 | CHMeCN | H | CF₃ | H | Cl | 167° C. |
| 113 | CHMeSAc | H | CF₃ | H | Cl | 115 to 118° C. |

TABLE 1-continued

| No. | R¹ | X¹ | X² | X³ | X⁴ | Physical properties |
|---|---|---|---|---|---|---|
| 114 | CMe₂Br | H | CF₃ | H | Cl | 89° C. |
| 115 | CHMeNHAc | H | CF₃ | H | Cl | 185 to 188° C. |
| 116 | CH=CH₂ | H | CF₃ | H | Cl | |
| 117 | CHMeOMe | H | CF₃ | H | Cl | Oil |
| 118 | CHMeSMe | H | CF₃ | H | Cl | |
| 119 | Me | H | CF(CF₃)₂ | H | Cl | |
| 120 | 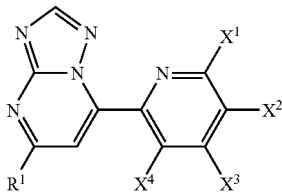 | H | CF₃ | H | I | |
| 121 | i-Pr | H | CF₃ | H | I | |
| 122 | Me | CF₃ | Cl | H | Cl | Solid |
| 123 | CH₂F | H | CF₃ | H | Cl | amorphous |

TABLE 2

| No. | ¹H-NMR δppm (Solvent: CDCl₃/400 MHz) |
|---|---|
| 4 | 7.28 (1H, d, J = 4.4 Hz), 8.38 (1H, d, J = 0.8 Hz), 8.56 (1H, s), 9.02 (1H, m), 9.02 (1H, s) |
| 5 | 7.43 (1H, d, J = 4.4 Hz), 7.97 (1H, dd, J = 8.8, 1.6 Hz), 8.56 (1H, s), 8.96 (1H, m), 9.03 (1H, d, J = 4.4 Hz) |
| 7 | 0.95 (9H, s), 7.33 (1H, d, J = 4.4 Hz), 8.16 (1H, d, J = 1.6 Hz), 8.56 (1H, s), 8.94 (1H, m), 8.99 (1H, d, J = 4.4 Hz) |
| 12 | 7.30 (1H, d, J = 4.4 Hz), 8.22 (1H, s), 8.56 (1H, s), 8.99 (1H, s), 9.02 (1H, d, J = 4.4 Hz) |
| 13 | 2.49 (3H, S), 7.27 (1H, d, J = 4.4 Hz), 7.79 (1H, s), 8.54 (1H, s), 8.56 (1H, s), 8.96 (1H, d, J = 4.4 Hz) |
| 14 | 7.44 (1H, d, J = 4.4 Hz), 8.51 (1H, s), 8.61 (1H, s), 9.07 (1H, d, J = 4.4 Hz), 9.29 (1H, s) |
| 16 | 1.47 (3H, t, J = 8.0 Hz), 3.09 (2H, q, J = 8.0 Hz), 7.17 (1H, s), 8.21 (1H, d, J = 1.6 Hz), 8.47 (1H, s), 8.98 (1H, m) |
| 17 | 1.07 (3H, t, J = 7.6 Hz), 1.95 (2H, m), 3.03 (2H, q, J = 7.6 Hz), 7.15 (1H, s), 8.22 (1H, s), 8.47 (1H, s), 8.98 (1H, m) |
| 18 | 2.84 (3H, s), 8.02 (1H, s), 8.22 (1H, d, J = 8.4 Hz), 8.57 (1H, s), 8.90 (1H, s), 9.34 (1H, d, J = 8.4 Hz) |
| 20 | 7.63 (1H, s), 8.23 (1H, s), 8.68 (1H, s), 8.98 (1H, s) |
| 43 | 2.86 (3H, s), 7.29 (1H, s), 8.50 (1H, s), 8.51 (1H, s), 9.27 (1H, s) |
| 48 | 3.56 (3H, s), 4.79 (2H, s), 7.55 (1H, s), 8.21 (1H, s), 8.51 (1H, s), 8.98 (1H, d, J = 0.8 Hz) |
| 52 | 2.72 (3H, s), 7.03 (1H, s), 7.16-7.30 (5H, m), 8.19 (1H, s), 8.25 (1H, s), 9.07 (1H, s) |
| 53 | 4.79 (2H, s), 7.49 (1H, s), 8.16 (1H, s), 8.48 (1H, s), 8.92 (1H, s) |
| 54 | 6.81 (1H, s), 7.76 (1H, s), 8.21 (1H, s), 8.56 (1H, s), 8.97 (1H, s) |
| 57 | 2.81 (3H, s), 7.02 (1H, s), 8.22 (1H, s), 8.41 (1H, s), 8.94 (1H, s) |
| 58 | 2.67 (3H, s), 2.83 (3H, s), 7.37 (1H, s), 8.34 (1H, s), 8.40 (1H, s), 9.13 (1H, s) |
| 60 | 4.67 (2H, s), 7.46 (1H, s), 8.20 (1H, s), 8.52 (1H, s), 8.96 (1H, s) |
| 62 | 6.71 (1H, s), 7.83 (1H, s), 8.22 (1H, s), 8.56 (1H, s), 8.99 (1H, s) |
| 63 | 3.98-4.04 (2H, m), 4.94 (2H, s), 7.46 (1H, s), 8.15 (1H, s), 8.44 (1H, s), 8.91 (1H, s) |
| 65 | 2.33 (6H, s), 3.78 (2H, s), 7.59 (1H, s), 8.17 (1H, s), 8.45 (1H, s), 8.94 (1H, s) |
| 66 | 2.37 (3H, s), 2.73 (2H, t, J = 4.8 Hz), 3.68 (2H, t, J = 4.8 Hz), 3.94 (2H, s), 7.50 (1H, s), 8.18 (1H, s), 8.45 (1H, s), 8.94 (1H, s) |
| 67 | 2.83 (3H, s), 7.06 (1H, s), 8.42 (1H, s), 8.51 (1H, s) |
| 72 | 1.21 (2H, s), 3.58 (2H, s), 4.08 (3H, s), 7.42 (1H, s), 8.17 (1H, s), 8.47 (1H, s), 8.93 (1H, s) |
| 73 | 5.12 (2H, s), 7.48 (1H, s), 8.14 (1H, s), 8.45 (1H, s), 8.89 (1H, s) |
| 74 | 2.38 (3H, s), 2.74 (2H, t, J = 5.2 Hz), 3.29 (3H, s), 3.51 (2H, t, J = 5.2 Hz), 3.93 (2H, s), 7.66 (1H, s), 8.17 (1H, s), 8.45 (1H, s), 8.95 (1H, s) |
| 75 | 2.52 (3H, s), 3.66 (2H, s), 4.08 (2H, s), 7.46 (1H, s), 8.19 (1H, s), 8.49 (1H, s), 8.96 (1H, s) |
| 76 | 2.58 (4H, m), 3.72 (4H, m), 3.86 (2H, s), 7.60 (1H, s), 8.19 (1H, s), 8.46 (1H, s), 8.96 (1H, s) |
| 77 | 3.81 (2H, d, J = 6.8 Hz), 4.82 (1H, t, J = 6.8 Hz), 7.30 (1H, s), 8.19 (1H, s), 8.51 (1H, s), 8.92 (1H, s) |
| 78 | 2.85 (3H, s), 7.41 (1H, s), 8.37 (1H, s), 8.84 (1H, s), 9.28 (1H, s) |
| 79 | 1.20 (3H, t, J = 7.2 Hz), 2.57 (2H, q, J = 7.2 Hz), 2.82 (3H, s), 7.10 (1H, s), 8.05 (1H, s), 8.46 (1H, s), 8.89 (1H, s) |
| 81 | 0.97 (6H, d, J = 6.8 Hz), 2.27 (1H, m), 2.84 (2H, d, J = 7.2 Hz), 7.01 (1H, s), 8.15 (1H, s), 8.40 (1H, s), 8.91 (1H, s) |
| 83 | 0.94 (3H, t, J = 7.2 Hz), 1.42 (2H, m), 1.85 (2H, m), 3.00 (2H, t, J = 7.6 Hz), 7.11 (1H, s), 8.17 (1H, s), 8.42 (1H, s), 8.93 (1H, s) |
| 87 | 0.88 (3H, t, J = 7.6 Hz), 1.36 (3H, d, J = 7.2 Hz), 1.69 (1H, m), 1.85 (1H, m), 3.00 (1H, m), 7.07 (1H, s), 8.14 (1H, s), 8.39 (1H, s), 8.90 (1H, s) |
| 89 | 1.42 (9H, s), 7.29 (1H, s), 8.15 (1H, s), 8.39 (1H, s), 8.91 (1H, s) |
| 90 | 7.20 (1H, dd, J = 4.0 Hz, J = 4.4 Hz), 7.56 (1H, s), 7.64 (1H, d, J = 4.4 Hz), 7.86 (1H, d, J = 4.0 Hz), 8.20 (1H, s), 8.45 (1H, s), 8.98 (1H, s) |
| 99 | 1.94-2.56 (6H, m), 3.83 (1H, m), 7.08 (1H, s), 8.17 (1H, s), 8.43 (1H, s), 8.93 (1H, s) |
| 102 | 1.53 (3H, d, J = 7.2 Hz), 4.15 (1H, q, J = 7.2 Hz), 4.81 (1H, s), 7.74 (1H, s), 8.58 (1H, s), 8.59 (1H, s), 9.07 (1H, s) |
| 104 | 1.86 (3H, dd, J = 6.8 Hz, J = 24.4 Hz), 5.87 (1H, dq, J = 6.8 Hz, J = 48.4 Hz), 7.56 (1H, s), 8.23 (1H, s), 8.54 (1H, s), 8.99 (1H, s) |
| 105 | 2.83 (3H, s), 7.14 (1H, s), 8.29 (1H, d, J = 0.8 Hz), 8.48 (1H, s) |
| 107 | 1.71-2.21 (8H, m), 3.40 (1H, m), 7.14 (1H, s), 8.17 (1H, s), 8.43 (1H, s), 8.94 (1H, s) |

TABLE 2-continued

| No. | $^1$H-NMR δppm (Solvent: CDCl$_3$/400 MHz) |
|---|---|
| 110 | 0.90 (3H, t, J = 7.2 Hz), 1.17 (2H, m), 1.37 (2H, m), 2.16 (1H, m), 4.01 (2H, q, J = 7.2 Hz), 7.19 (1H, s), 8.22 (1H, s), 8.59 (1H, s), 9.07 (1H, s) |
| 117 | 1.60 (3H, d, J = 7.2 Hz), 3.43 (3H, s), 4.64 (1H, q, J = 7.2 Hz), 7.53 (1H, s), 8.22 (1H, s), 8.51 (1H, s), 8.99 (1H, s) |
| 122 | 2.82 (3H, s), 7.15 (1H, s), 8.17 (1H, s), 8.44 (1H, s) |
| 123 | 5.71 (2H, d, J = 46.8 Hz), 7.53 (1H, s), 8.23 (1H, s), 8.55 (1H, s), 9.00 (1H, s) |

TABLE 3

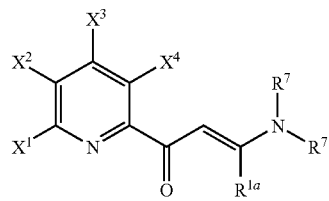

| No. | R$^{1a}$ | X$^1$ | X$^2$ | X$^3$ | X$^4$ | R$^7$ | Physical properties |
|---|---|---|---|---|---|---|---|
| IV-1 | Me | H | CF$_3$ | H | Cl | Me | 83 to 86° C. |
| IV-2 | Me | H | H | H | CF$_3$ | Me | solid |
| IV-3 | Et | H | CF$_3$ | H | Cl | Me | 74 to 76° C. |
| IV-4 | n-Pr | H | CF$_3$ | H | Cl | Me | 127 to 129° C. |
| IV-5 | H | H | CF$_3$ | H | H | Me | 57 to 60° C. |
| IV-6 | H | H | H | H | CF$_3$ | Me | oil |
| IV-7 | H | H | CF$_3$ | H | Br | Me | 102 to 104° C. |
| IV-8 | H | H | Cl | H | Cl | Me | oil |
| IV-9 | Me | H | CF$_3$ | H | Br | Me | 110 to 112° C. |
| IV-10 | H | H | H | CF$_3$ | H | Me | oil |
| IV-11 | H | Cl | H | CF$_3$ | H | Me | solid |
| IV-12 | H | Cl | Cl | CF$_3$ | Cl | Me | solid |
| IV-13 | H | H | NO$_2$ | H | Cl | Me | oil |
| IV-14 | H | H | CF$_3$ | H | NO$_2$ | Me | oil |
| IV-15 | H | H | Me | H | Cl | Me | oil |
| IV-16 | CH$_2$OMe | H | CF$_3$ | H | Cl | Me | oil |
| IV-17 | Me | CF$_3$ | H | H | CF$_3$ | Me | oil |
| IV-18 | Me | NMe$_2$ | CF$_3$ | H | Cl | Me | oil |
| IV-19 | Me | Cl | CF$_3$ | H | CF$_3$ | Me | 113 to 115° C. |
| IV-20 | Me | Cl | CF$_3$ | H | Cl | Me | 108 to 110° C. |
| IV-21 | Me | OMe | CF$_3$ | H | Cl | Me | 101 to 102° C. |
| IV-22 | Me | H | CF$_3$ | H | I | Me | 120 to 123° C. |
| IV-23 | Me | Cl | CF$_3$ | H | F | Me | 88 to 92° C. |

TABLE 4

| No. | $^1$H-NMR δppm (Solvent: CDCl$_3$/400 MHz) |
|---|---|
| IV-6 | 2.92 (3H, broad signal), 3.14 (3H, broad signal), 5.56 (1H, broad d), 7.25-7.46 (1H, m), 7.85 (1H, broad signal), 8.04 (1H, dd, J = 7.6, 0.8 Hz), 8.75 (1H, dd, J = 4.8, 0.8 Hz) |
| IV-8 | 2.92 (3H, broad signal), 3.14 (3H, broad signal), 5.59 (1H, broad signal), 7.77 (1H, d, J = 2 Hz), 8.45 (1H, J = 2 Hz) |
| IV-10 | 3.01 (3H, s), 3.21 (3H, s), 6.46 (1H, d, J = 12.8 Hz), 7.57 (1H, d, J = 4.8 Hz), 7.96 (1H, d, J = 12.8 Hz), 8.40 (1H, s), 8.80 (1H, d, J = 4.8 Hz) |
| IV-11 | 3.04 (3H, s), 3.22 (3H, s), 6.40 (1H, d, J = 12.8 Hz), 7.61 (1H, s), 7.96 (1H, d, J = 12.8 Hz), 8.31 (1H, s) |
| IV-12 | 2.93 (3H, s), 3.18 (3H, broad signal), 5.35 (1H, d, J = 12.8 Hz), 7.88 (1H, broad signal) |
| IV-13 | 2.95 (3H, s), 3.20 (3H, broad signal), 5.55 (1H, broad d), 7.93 (1H, broad signal), 8.54 (1H, d, J = 2.2 Hz), 9.29 (1H, d, J = 2.2 Hz) |
| IV-14 | 2.94 (3H, s), 3.17 (3H, broad signal), 5.56 (1H, broad d), 7.95 (1H, broad signal), 7.99 (1H, s), 8.74 (1H, s) |
| IV-15 | 2.36 (3H, s), 2.91 (3H, s), 3.16 (3H, broad signal), 5.61 (1H, broad signal), 7.57 (1H, d, J = 0.8 Hz), 7.90 (1H, broad signal), 8.31 (1H, d, J = 2.2 Hz) |
| IV-16 | 3.00 (3H, broad signal), 3.20 (3H, broad signal), 3.49 (3H, s), 5.08 (2H, s), 5.46 (1H, s), 7.96 (1H, d, J = 1.2 Hz), 8.72 (1H, dd, J = 0.8, 2.0 Hz) |
| IV-17 | 2.69 (3H, s), 3.09 (6H, broad signal), 5.44 (1H, s), 7.76 (1H, d, J = 7.6 Hz), 8.20 (1H, d, J = 7.6 Hz) |
| IV-18 | 2.70 (3H, s), 3.02 (6H, s), 3.07 (6H, s), 5.46 (1H, s), 7.78 (1H, s) |

TABLE 5

| No. | R$^{1c}$ | X$^1$ | X$^2$ | X$^3$ | X$^4$ | Physical properties |
|---|---|---|---|---|---|---|
| IX-1 | N-methylpyrrol-2-yl | H | CF$_3$ | H | Cl | |
| IX-2 | thiazol-2-yl | H | CF$_3$ | H | Cl | |
| IX-3 | thien-2-yl | H | CF$_3$ | H | Cl | 47° C. |
| IX-4 | furan-2-yl | H | CF$_3$ | H | Cl | 50° C. |
| IX-5 | pyridin-2-yl | H | CF$_3$ | H | Cl | |
| IX-6 | pyridin-4-yl | H | CF$_3$ | H | Cl | |
| IX-7 | Et | H | CF$_3$ | H | Cl | |
| IX-8 | Me | H | CF$_3$ | H | Cl | 51° C. |
| IX-9 | cyclopropyl | H | CF$_3$ | H | Cl | |
| IX-10 | n-Bu | H | CF$_3$ | H | Cl | |
| IX-11 | i-Pr | H | CF$_3$ | H | Cl | |
| IX-12 | i-Bu | H | CF$_3$ | H | Cl | |
| IX-13 | Ph | H | CF$_3$ | H | Cl | |
| IX-14 | CH$_2$CH$_2$(i-Pr) | H | CF$_3$ | H | Cl | |

TABLE 5-continued

| No. | $R^{1c}$ | $X^1$ | $X^2$ | $X^3$ | $X^4$ | Physical properties |
|---|---|---|---|---|---|---|
| IX-15 | sec-Bu | H | $CF_3$ | H | Cl | |
| IX-16 | t-Bu | H | $CF_3$ | H | Cl | |
| IX-17 | $CH_2$(t-Bu) | H | $CF_3$ | H | Cl | |
| IX-18 |  | H | $CF_3$ | H | Cl | |
| IX-19 |  | H | $CF_3$ | H | Cl | |
| IX-20 |  | H | $CF_3$ | H | Cl | |
| IX-21 |  | H | $CF_3$ | H | Cl | |
| IX-22 | i-Pr | H | $CF_3$ | H | Br | |
| IX-23 |  | H | $CF_3$ | H | Br | |
| IX-24 |  | H | $CF_3$ | H | $CO_2Et$ | |
| IX-25 | $CF_3$ | H | $CF_3$ | H | Cl | |

TABLE 6

| No. | $^1$H-NMR δppm (Solvent: $CDCl_3$/400 MHz) |
|---|---|
| IX-7 | 1.22 (3H, t, J = 7.2 Hz), 2.48 (2H, q, J = 7.2 Hz), 6.28 (1H, s), 8.02 (1H, s), 8.77 (1H, s) |
| IX-9 | 0.86-0.89 (2H, m), 1.29 (3H, s), 1.36-1.41 (2H, m), 6.33 (1H, s), 8.01 (1H, s), 8.78 (1H, s) |
| IX-18 | 0.94-1.07 (2H, m), 1.21-1.25 (2H, m), 1.80 (1H, m), 6.37 (1H, s), 8.01 (1H, s), 8.78 (1H, s) |

Now, Test Examples will be described.

Test Example 1

Test on Controlling Effects Against Green Peach Aphid (*Myzus persicae*)

A Japanese radish leaf was inserted in a test tube in which water was put, and about 20 first instar nymphs of green peach aphid were released on the leaf. On the next day, the number of nymphs parasitic on the leaf was counted, and then the leaf was dipped for about 10 seconds in an insecticidal solution prepared to bring the concentration of the compound of the present invention to 200 ppm, dried in air and left in a constant temperature chamber at 25° C. with lightening. Dead nymphs were counted 5 days after the treatment, and the mortality was calculated by the following equation. The insects dropped from the leaf or presented toxic symptom were counted as dead insects. The test was carried out with respect to the above-mentioned compound Nos. 4, 15, 16, 17, 18, 19, 20, 41, 43, 44, 48, 51, 53, 68, 73, 78, 79, 80, 82, 94, 95 and 104, whereby all compounds showed a mortality of at least 90%.

Mortality (%)=(1−(number of survived insects/number of treated insects))×100

Test Example 2

Test on Controlling Effects Against Brown Planthopper (*Nilaparvata lugens*)

Rice seedling was dipped for about 10 seconds in an insecticidal solution prepared to bring the concentration of the compound of the present invention to 200 ppm and then dried in air, its root was wrapped with a wet absorbent cotton, and the seedling was put into a test tube. Then, 10 second-third instar nymphs of Brown Planthopper were released therein, and the test tube was covered with a gauze and left in a constant temperature chamber at 25° C. with lightening. On the 5th day after the release, dead nymphs were counted, and the mortality was calculated by the following equation.

The test was carried out with respect to the above-mentioned Compound Nos. 4, 12, 15, 16, 17, 19, 20, 41, 43, 44, 48, 52, 57, 68, 70, 75, 79, 80, 81, 82, 83, 87, 89, 91, 94, 95, 98, 99, 104, 105 and 107, whereby all compounds showed a mortality of at least 90%.

Mortality (%)=(number of dead insects/number of released insects)×100

Test Example 3

Test on Controlling Effects Against Silverleaf Whitefly (*Bemisia Argentifolii*)

An insecticidal solution prepared to bring the concentration of the compound of the present invention to 200 ppm was applied by a hand spray to cucumber seedling planted in a pot on which first-second instar nymphs of silverleaf whitefly were parasitic, and dried in air. Thereafter, the cucumber seedling was left in a constant temperature chamber at 25° C. with lightening. The number of old instar nymphs was counted 7 days after the treatment, and the protective value (%) was obtained by the following equation. The test was carried out with respect to the above-mentioned compound Nos. 4, 5, 12, 14, 15, 16, 17, 18, 19, 20, 44, 48, 80, 82 and 94, whereby all the compounds showed a protective value of at least 80%.

Protective value (%)=(1−((Ta×Cb)/(Tb×Ca)))×100

Ta: The number of old instar nymphs after the treatment at the treated cucumber seedling
Tb: The number of first-second instar nymphs before the treatment at the treated cucumber seedling
Ca: The number of old instar nymphs after the treatment at the untreated cucumber seedling
Cb: the number of first-second instar nymphs before the treatment at the untreated cucumber seedling

Test Example 4

Pesticidal Test Against *Haemaphysalis longicornis* Employing a Dog

A gelatin capsule containing the compound of the present invention at a dose of 10 mg/kg weight is applied to a dog (Beagle, 8 months old), and immediately after the application, about 50 young mites of *Haemaphysalis longicornis* are released on the auricle of the dog and artificially parasitized. After the treatment, observation is carried out to inspect the parasitic number, the fallen number and the mortality of the fallen *Haemaphysalis longicornis*. As a result, the compound of the present invention is effective to have the parasitized *Haemaphysalis longicornis* fallen or dead.

Test Example 5

Pesticidal Test Against Cat Flea (*Ctenocephalides felis*) Employing a Dog

A gelatin capsule containing the compound of the present invention at a dose of 10 mg/kg weight is applied to a dog (Beagle, 8 months old), and immediately after the application, about 100 non-bloodsucked adults of cat flea are released on the dorsal fur of the dog and artificially parasitized. After the treatment, the cat flea is recovered by means of a flea catching comb, and the parasitized number is counted. As a result, the compound of the present invention is effective to control the parasitizing of cat flea.

Now, Formulation Examples are described below.

Formulation Example 1

| | |
|---|---|
| (1) Compound of the present invention | 20 parts by weight |
| (2) Clay | 70 parts by weight |
| (3) White carbon | 5 parts by weight |
| (4) Sodium polycarboxylate | 3 parts by weight |
| (5) Sodium alkylnaphthalene sulfonate | 2 parts by weight |

The above components are uniformly mixed to obtain a wettable powder.

Formulation Example 2

| | |
|---|---|
| (1) Compound of the present invention | 5 parts by weight |
| (2) Talc | 60 parts by weight |
| (3) Calcium carbonate | 34.5 parts by weight |
| (4) Liquid paraffin | 0.5 part by weight |

The above components are uniformly mixed to obtain a dust.

Formulation Example 3

| | |
|---|---|
| (1) Compound of the present invention | 20 parts by weight |
| (2) N,N-dimethylacetamide | 20 parts by weight |
| (3) Polyoxyethylene tristyryl phenyl ether | 10 parts by weight |
| (4) Calcium dodecylbenzene sulfonate | 2 parts by weight |
| (5) Xylene | 48 parts by weight |

The above components are uniformly mixed and dissolved to obtain an emulsifiable concentrate.

Formulation Example 4

| | |
|---|---|
| (1) Clay | 68 parts by weight |
| (2) Sodium lignin sulfonate | 2 parts by weight |
| (3) Polyoxyethylenealkylaryl sulfate | 5 parts by weight |
| (4) White carbon | 25 parts by weight |

The mixture of the above components is mixed with compound of the present invention in a weight ratio of 4:1 to obtain a wettable powder.

Formulation Example 5

| | |
|---|---|
| (1) Compound of the present invention | 50 parts by weight |
| (2) Sodium alkylnaphthalene sulfonate condensation product of formaldehyde | 2 parts by weight |
| (3) Silicone oil | 0.2 part by weight |
| (4) Water | 47.8 parts by weight |
| The above components are uniformly mixed and pulverized to obtain a base liquid, and | |
| (5) Sodium polycarboxylate | 5 parts by weight |
| (6) Anhydrous sodium sulfate | 42.8 parts by weight |
| are added, and the mixture is uniformly mixed, granulated and dried to obtain water-dispersible granules. | |

Formulation Example 6

| | |
|---|---|
| (1) Compound of the present invention | 5 parts by weight |
| (2) Polyoxyethyleneoctylphenyl ether | 1 part by weight |
| (3) Polyoxyethylene alkyl ether phosphoric acid ester | 0.1 part by weight |
| (4) Granular calcium carbonate | 93.9 parts by weight |

The above components (1) to (3) are preliminarily uniformly mixed and diluted with a proper amount of acetone, and then the mixture is sprayed onto the component (4), and acetone is removed to obtain granules.

Formulation Example 7

| | |
|---|---|
| (1) Compound of the present invention | 2.5 parts by weight |
| (2) N,N-dimethylacetamide | 2.5 parts by weight |
| (3) Soybean oil | 95.0 parts by weight |

The above components are uniformly mixed and dissolved to obtain an ultra low volume formulation.

Formulation Example 8

| | |
|---|---|
| (1) Compound of the present invention | 40 parts by weight |
| (2) Potassium polyoxyethylene styryl phenyl ether phosphate | 4 parts by weight |
| (3) Silicone oil | 0.2 part by weight |
| (4) Xanthan gum | 0.1 part by weight |
| (5) Ethylene glycol | 5 parts by weight |
| (6) Water | 50.7 parts by weight |

The above components are uniformly mixed and pulverized to obtain a water-based suspension concentrate.

Formulation Example 9

| | |
|---|---|
| (1) Compound of the present invention | 10 parts by weight |
| (2) Diethylene glycol monoethyl ether | 80 parts by weight |
| (3) Polyoxyethylenealkyl ether | 10 parts by weight |

The above components are uniformly mixed to obtain a soluble concentrate.

INDUSTRIAL APPLICABILITY

The pesticide containing a novel pyridyl-triazolopyrimidine derivative or its salt as an active ingredient of the present invention is excellent in the effect, the dosage, etc. as compared with conventional products, and has a very high controlling effect with a low dosage and is thereby applicable to control of pests, and particularly it is highly industrially applicable as an agricultural and horticultural pesticide and as a pesticide against parasites on animals.

The entire disclosure of Japanese Patent Application No. 2007-34371 filed on Feb. 15, 2007 including specification, claims, drawings and summary is incorporated herein by reference in its entirety.

The invention claimed is:

1. A compound represented by the formula (I) or its salt:

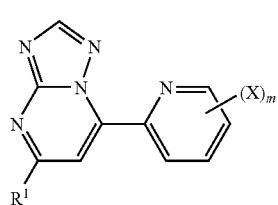

(I)

wherein
R$^1$ is hydrogen, alkyl which may be substituted by A, cycloalkyl which may be substituted by A, alkenyl which may be substituted by A, alkynyl which may be substituted by A, halogen, cyano, aryl, OR$^2$, S(O)$_n$R$^3$, NR$^4$R$^5$ or a heterocyclic group which may be substituted by alkyl;
R$^2$ is hydrogen, alkyl, alkenyl, alkynyl, haloalkyl, alkoxyalkyl, acetyl or aryl;
R$^3$ is alkyl or acetyl;
R$^4$ is hydrogen or alkyl;
R$^5$ is hydrogen, alkyl, acetyl, CH$_2$CH$_2$OR$^2$ or CH$_2$CN;
A is halogen, OR$^2$, S(O)$_n$R$^3$, NR$^4$R$^5$, cyano, alkyl, cycloalkyl, aryl, a heterocyclic group, SCH$_2$COOR$^2$ or —CH(CN)$_2$;
X is alkyl, alkenyl, alkynyl, aryl, halogen, haloalkyl, cyano, nitro, NR$^4$R$^5$, S(O)$_n$R$^3$, COR$^2$ or COOR$^2$;
m is an integer of from 1 to 4; and
n is an integer of from 0 to 2;
provided that 7-(3-chloro-5-(trifluoromethyl)pyridin-2-yl)-[1,2,4]-triazolo[1,5-a]pyrimidine is excluded.

2. The compound or its salt according to claim 1, wherein R$^1$ is hydrogen, alkyl which may be substituted by A, cycloalkyl which may be substituted by A, alkenyl which may be substituted by A, alkynyl which may be substituted by A, halogen, cyano, aryl, OR$^2$, S(O)$_n$R$^3$, NR$^4$R$^5$ or a heterocyclic group;
R$^2$ is hydrogen, alkyl, alkenyl, alkynyl, haloalkyl or aryl;
R$^3$ is alkyl;
R$^5$ is hydrogen or alkyl;
A is halogen, OR$^2$, S(O)$_n$R$^3$, NR$^4$R$^5$, cyano, cycloalkyl, aryl or a heterocyclic group; and
X is alkyl, alkenyl, alkynyl, halogen, haloalkyl, cyano or nitro.

3. The compound or its salt according to claim 2, wherein R$^1$ is hydrogen, alkyl, haloalkyl, cycloalkyl, alkenyl, alkynyl, halogen, cyano, aryl, OR$^2$, S(O)$_n$R$^3$, NR$^4$R$^5$ or a heterocyclic group.

4. The compound or its salt according to claim 3, wherein R$^1$ is hydrogen, alkyl, haloalkyl, alkynyl, cyano, aryl, OR$^2$, S(O)$_n$R$^3$, NR$^4$R$^5$ or a heterocyclic group.

5. The compound or its salt according to claim 2, wherein R$^1$ is alkyl which may be substituted by A, cycloalkyl which may be substituted by A, alkenyl which may be substituted by A, alkynyl which may be substituted by A, halogen, cyano, aryl, OR$^2$, S(O)$_n$R$^3$, NR$^4$R$^5$ or a heterocyclic group.

6. The compound or its salt according to claim 5, wherein R$^1$ is alkyl, haloalkyl, cycloalkyl, alkenyl, alkynyl, cyano, aryl, OR$^2$, S(O)$_n$R$^3$, NR$^4$R$^5$ or a heterocyclic group.

7. The compound or its salt according to claim 6, wherein R$^1$ is alkyl, haloalkyl, cycloalkyl or alkenyl.

8. The compound or its salt according to claim 5, wherein R$^1$ is alkyl, haloalkyl, alkynyl, cyano, aryl, OR$^2$, S(O)$_n$R$^3$, NR$^4$R$^5$ or a heterocyclic group.

9. A process for producing a compound represented by the formula (I) or its salt:

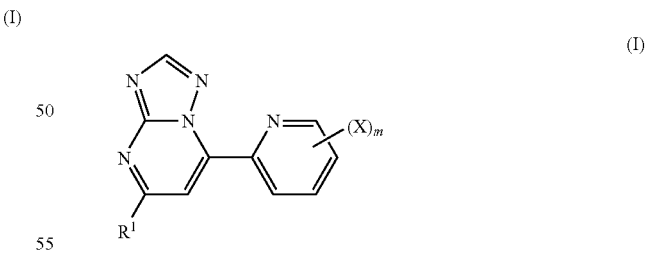

(I)

wherein
R$^1$ is hydrogen, alkyl which may be substituted by A, cycloalkyl which may be substituted by A, alkenyl which may be substituted by A, alkynyl which may be substituted by A, halogen, cyano, aryl OR$^2$, S(O)$_n$R$^3$, NR$^4$R$^5$ or a heterocyclic group which may be substituted by alkyl;
R$^2$ is hydrogen, alkyl, alkenyl, alkynyl, haloalkyl, alkoxyalkyl, acetyl or aryl;
R$^3$ is alkyl or acetyl;
R$^4$ is hydrogen or alkyl;

$R^5$ is hydrogen, alkyl, acetyl, $CH_2CH_2OR^2$ or $CH_2CN$;

A is halogen, $OR^2$, $S(O)_nR^3$, $NR^4R^5$, cyano, alkyl, cycloalkyl, aryl, a heterocyclic group, $SCH_2COOR^2$ or —$CH(CN)_2$;

X is alkyl, alkenyl, alkynyl, aryl, halogen, haloalkyl, cyano, nitro, $NR^4R^5$, $S(O)_nR^3$, $COR^2$ or $COOR^2$;

m is an integer of from 1 to 4; and n is an integer of from 0 to 2;

provided that 7-(3-chloro-5-(trifluoromethyl)pyridin-2-yl)-[1,2,4]triazolo[1,5-a]pyrimidine is excluded, which comprises (1) condensing an α,β-unsaturated ketone derivative represented by the formula (IV):

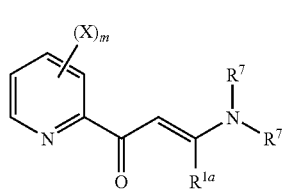

(IV)

wherein X and m are as defined above, $R^{1a}$ is hydrogen, alkyl which may be substituted by A, cycloalkyl which may be substituted by A, alkenyl which may be substituted by A, alkynyl which may be substituted by A, aryl or a heterocyclic group which may be substituted by alkyl, and $R^7$ is alkyl, and a compound represented by the formula (V):

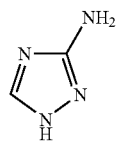

(V)

(2) condensing an α,β-unsaturated ketone derivative represented by the formula (VII):

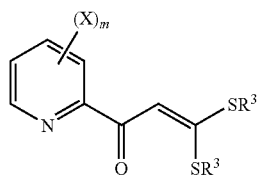

(VII)

wherein $R^3$, X and m are as defined above, and the compound of the above formula (V);

(3) oxidizing a compound represented by the formula (I-2):

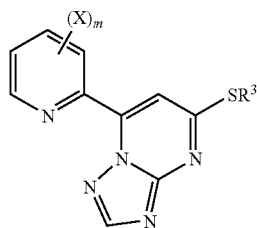

(I-2)

wherein $R^3$, X and m are as defined above;

(4) reacting a compound represented by the formula (I-3):

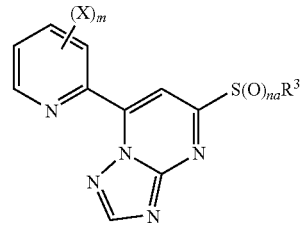

(I-3)

wherein $R^3$, X and m are as defined above, and na is an integer of from 1 to 2, with a nucleophilic reagent;

(5) condensing a compound represented by the formula (IX):

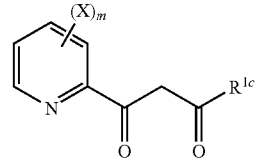

(IX)

wherein X and m are as defined above, and $R^{1c}$ is alkyl which may be substituted by A, cycloalkyl which may be substituted by A, alkenyl which may be substituted by A, alkynyl which may be substituted by A, aryl or a heterocyclic group which may be substituted by alkyl, and the compound of the above formula (V); or (6) halogenating a 4,5-dihydro-5-oxo[1,2,4]triazolo[1,5-a]pyrimidine derivative represented by the formula (XV):

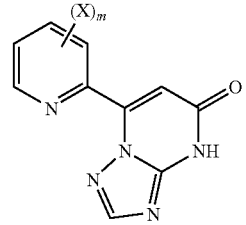

(XV)

wherein X and m are as defined above.

10. A process for producing a compound represented by the formula (I-1) or its salt:

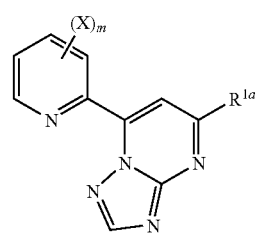

(I-1)

wherein
R$^{1a}$ is hydrogen, alkyl which may be substituted by A, cycloalkyl which may be substituted by A, alkenyl which may be substituted by A, alkynyl which may be substituted by A, aryl or a heterocyclic group which may be substituted by alkyl;
X is alkyl, alkenyl, alkynyl, aryl, halogen, haloalkyl, cyano, nitro, NR$^4$R$^5$, S(O)$_n$R$^3$, COR$^2$ or COOR$^2$;
R$^2$ is hydrogen, alkyl, alkenyl, alkynyl, haloalkyl, alkoxyalkyl, acetyl or aryl;
R$^3$ is alkyl or acetyl;
R$^4$ is hydrogen or alkyl;
R$^5$ is hydrogen, alkyl, acetyl, CH$_2$CH$_2$OR$^2$ or CH$_2$CN; A is halogen, OR$^2$, S(O)$_n$R$^3$, NR$^4$R$^5$, cyano, alkyl, cycloalkyl, aryl, a heterocyclic group, SCH$_2$COOR$^2$ or —CH(CN)$_2$;
m is an integer of from 1 to 4; and
n is an integer of from 0 to 2;
provided that 7-(3-chloro-5-(trifluoromethyl)pyridin-2-yl)-[1,2,4]triazolo[1,5-a]pyrimidine is excluded, which comprises condensing a compound represented by the formula (II):

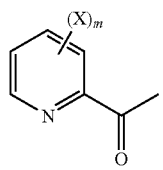
(II)

wherein X and m are as defined above, and a compound represented by the formula

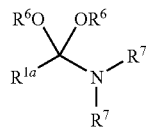
(III)

wherein R$^{1a}$ is as defined above; and each of R$^6$ and R$^7$ which are independent of each other, is alkyl, to obtain an α,β-unsaturated ketone derivative represented by the formula (IV):

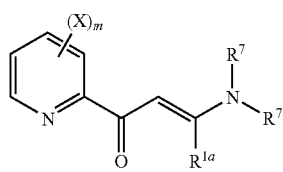
(IV)

wherein R$^{1a}$, R$^7$, X and m are as defined above, and condensing the obtained ketone derivative and a compound represented by the formula (V):

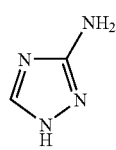
(V)

11. A process for producing a compound represented by the formula (I-5) or its salt:

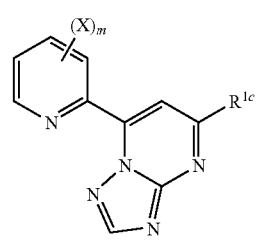
(I-5)

wherein
R$^{1c}$ is alkyl which may be substituted by A, cycloalkyl which may be substituted by A, alkenyl which may be substituted by A, alkynyl which may be substituted by A, aryl or a heterocyclic group which may be substituted by alkyl;
X is alkyl, alkenyl, alkynyl, aryl, halogen, haloalkyl, cyano, nitro, NR$^4$R$^5$, S(O)$_n$R$^3$, COR$^2$ or COOR$^2$;
R$^2$ is hydrogen, alkyl, alkenyl, alkynyl, haloalkyl, alkoxyalkyl, acetyl or aryl;
R$^3$ is alkyl or acetyl;
R$^4$ is hydrogen or alkyl;
R$^5$ is hydrogen, alkyl, acetyl, CH$_2$CH$_2$OR$^2$ or CH$_2$CN;
A is halogen, OR$^2$, S(O)$_n$R$^3$, NR$^4$R$^5$, cyano, alkyl, cycloalkyl, aryl, a heterocyclic group, SCH$_2$COOR$^2$ or —CH(CN)$_2$;
m is an integer of from 1 to 4; and
n is an integer of from 0 to 2, which comprises
(1) reacting a compound represented by the formula (II):

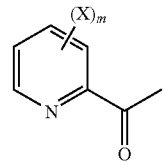
(II)

wherein X and m are as defined above, with a compound represented by the formula (VIII): R$^{1c}$CO$_2$R$^8$ (wherein R$^{1c}$ is as defined above; and R$^8$ is alkyl), or
(2) reacting a compound represented by the formula (X):

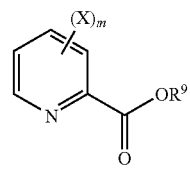
(X)

wherein X and m are as defined above; and R$^9$ is alkyl, with a compound represented by the formula (XVI):

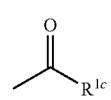
(XVI)

wherein R$^{1c}$ is as defined above, to obtain a compound represented by the formula (IX):
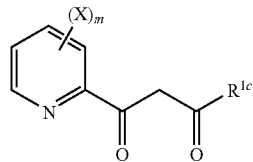
(IX)
wherein R$^{1c}$, X and m are as defined above, and
(3) condensing the compound of the above formula (IX) and a compound represented by the formula (V):
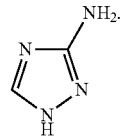
(V)
* * * * *